US011176359B2

United States Patent
Yabuki et al.

(10) Patent No.: US 11,176,359 B2
(45) Date of Patent: Nov. 16, 2021

(54) MOTION RECOGNITION DEVICE AND MOTION RECOGNITION METHOD

(71) Applicant: FUJITSU LIMITED, Kawasaki (JP)

(72) Inventors: Akihiko Yabuki, Isehara (JP); Yoshihiko Nakamura, Bunkyo (JP); Wataru Takano, Bunkyo (JP)

(73) Assignee: FUJITSU LIMITED, Kawasaki (JP)

( * ) Notice: Subject to any disclaimer, the term of this patent is extended or adjusted under 35 U.S.C. 154(b) by 53 days.

(21) Appl. No.: 16/362,701

(22) Filed: Mar. 25, 2019

(65) Prior Publication Data

US 2019/0220657 A1 Jul. 18, 2019

Related U.S. Application Data

(63) Continuation of application No. PCT/JP2017/036797, filed on Oct. 11, 2017.

(30) Foreign Application Priority Data

Oct. 11, 2016 (WO) .................. PCT/JP2016/080150

(51) Int. Cl.
*G06K 9/00* (2006.01)
*G06T 7/246* (2017.01)
(Continued)

(52) U.S. Cl.
CPC ........ *G06K 9/00342* (2013.01); *A61B 5/1122* (2013.01); *A61B 5/1128* (2013.01);
(Continued)

(58) Field of Classification Search
CPC ........... G06K 9/00342; G06K 9/00369; G06K 9/00751; G06K 9/00765; G06K 9/6267;
(Continued)

(56) References Cited

U.S. PATENT DOCUMENTS

2010/0303303 A1    12/2010  Shen et al.
2012/0143358 A1*    6/2012  Adams ............... G06K 9/00342
                                                                700/92
(Continued)

FOREIGN PATENT DOCUMENTS

CN    103310193 A    9/2013
WO    2012/112402 A2    8/2012
WO    2016/056449 A1    4/2016

OTHER PUBLICATIONS

Sato et al ("Kinematic Analysis of Basic Rhythmic Movements of Hip-hop Dance: Motion Characteristics Common to Expert Dancers", Journal of Applied Biomechanics, vol. 31 Issue 1, pp. 1-7, 2015 (Year: 2015).*

(Continued)

*Primary Examiner* — Leon Viet Q Nguyen

(74) *Attorney, Agent, or Firm* — Xsensus LLP

(57) ABSTRACT

A motion recognition device includes a memory, and a processor coupled to the memory and configured to classify a plurality of frames including positional information of a feature point that corresponds to a predetermined part or a joint part of a body of a subject into a plurality of groups in time series by segmenting the plurality of frames in time series based on a position of the predetermined part of the body of the subject, identify a type of a basic motion that corresponds to the group, based on movement of the feature point included in a consecutive frame, for each group, and evaluate a skill and a difficulty level of a motion performed (Continued)

by the subject based on an order of each type of the basic motion that corresponds to a group which is consecutive in time series.

12 Claims, 22 Drawing Sheets

(51) Int. Cl.

| | | |
|---|---|---|
| G06T 7/73 | (2017.01) | |
| G06T 7/00 | (2017.01) | |
| G06K 9/62 | (2006.01) | |
| A63B 5/12 | (2006.01) | |
| A63B 24/00 | (2006.01) | |
| A61B 5/11 | (2006.01) | |
| G06T 7/215 | (2017.01) | |
| G06T 7/20 | (2017.01) | |

(52) U.S. Cl.
CPC ............ *A63B 5/12* (2013.01); *A63B 24/0003* (2013.01); *A63B 24/0062* (2013.01); *G06K 9/00369* (2013.01); *G06K 9/00751* (2013.01); *G06K 9/00765* (2013.01); *G06K 9/6267* (2013.01); *G06T 7/0002* (2013.01); *G06T 7/20* (2013.01); *G06T 7/215* (2017.01); *G06T 7/246* (2017.01); *G06T 7/73* (2017.01); *A61B 2503/10* (2013.01); *A63B 2024/0071* (2013.01); *A63B 2220/05* (2013.01); *A63B 2220/20* (2013.01); *A63B 2220/806* (2013.01); *G06T 2207/30196* (2013.01); *G06T 2207/30221* (2013.01)

(58) Field of Classification Search
CPC ........... G06T 7/215; G06T 7/246; G06T 7/73; G06T 2207/30196; G06T 2207/30221; A61B 5/1122; A61B 5/1128; A61B 2503/10; A63B 5/12; A63B 24/0003; A63B 24/0062; A63B 2024/0071; A63B 2220/05; A63B 2220/20; A63B 2220/806
See application file for complete search history.

(56) References Cited

U.S. PATENT DOCUMENTS

2012/0214594 A1* 8/2012 Kirovski ............ G06K 9/00355
463/36
2017/0189784 A1 7/2017 Sasaki

OTHER PUBLICATIONS

Shin et al., "A Study on Motion Analysis of an Artistic Gymnastics by using Dynamic Image Processing", IEICE Technical Report, Recognition of Pattern and Understanding of Media, vol. 108, No. 46, May 15, 2008, 20 Including translation.
Shin et al., "A Study on Motion Analysis of an Artistic Gymnastics by using Dynamic Image Processing", IEEE International Conference on Systems, Man and Cybernetics, 2008, pp. 1037-1042.
Yoshimura et al., "A study of improve gesture recognition accuracy using machine learning", Game Programming Workshop 2012, Collection of Papers, Jun. 2012, pp. 167-170 (See English Abstract).
International Search Report dated Dec. 19, 2017 for PCT/JP2017/036797 filed on Oct. 11, 2017, 6 pages including English Translation.
Extended European Search Report dated Sep. 30, 2019, issued in corresponding European Application No. 178596l6.9, 13 pages.
Adrian Stoica et al.: "2013 Code of Points Men's Artistic Gymnastics", 2013, XP055622589, Lausanne, Switzerland, Retrieved from the Internet: URL:http://lapatriote.fr/wp-content/uploads/2014/10/CODE_FIG_2013-vl.pdf[retrieved on Sep. 16, 2019].
M. Pino Diaz-Pereira et al.: "Automatic recognition and scoring of Olympic rhythmic gymnastic movements", Human Movement Science, vol. 34, Feb. 4, 2014 (Feb. 4, 2014), pp. 63-80, XP055622891.
Brian Reily: "Pose Estimation of Gymnasts", EENG 512/CSCI 512 Final Projects, 2015, XP055623062, Golden, Colorado, Retrieved from the Internet: URL:https://inside.mines.edu/~whoff/courses/EENG512/projects/2015/Reily.pdf [retrieved on Sep. 17, 2019].
Anonymous: "Scoring Gymnastics Competitions More Accurately with 3D Sensing Technology—What Is the Future of Judging?", FUJITSU JOURNAL, Sep. 7, 2016 (Sep. 7, 2016), XP055622682, Retrieved from the Internet URL:https://journal.jp.fujitsu.com/en/2016/09/07/01/[retrieved on Sep. 16, 2019].
Communication pursuant to Article 94(3) EPC dated Apr. 28, 2021, in corresponding European Patent Application No. 17 859 616.9.

* cited by examiner

FIG. 5

| FRAME NUMBER | HAND AND FOOT POSITION DATA | BODY VECTOR DATA | SEGMENT NUMBER |
|---|---|---|---|
| 1 | "HAND AND FOOT POSITION" DATA CALCULATED FROM FRAME HAVING FRAME NUMBER "1" | "BODY VECTOR" DATA CALCULATED FROM FRAME HAVING FRAME NUMBER "1" | 1 |
| 2 | "HAND AND FOOT POSITION" DATA CALCULATED FROM FRAME HAVING FRAME NUMBER "2" | "BODY VECTOR" DATA CALCULATED FROM FRAME HAVING FRAME NUMBER "2" | 1 |
| 3 | "HAND AND FOOT POSITION" DATA CALCULATED FROM FRAME HAVING FRAME NUMBER "3" | "BODY VECTOR" DATA CALCULATED FROM FRAME HAVING FRAME NUMBER "3" | 1 |
| ... | | | |
| 10 | "HAND AND FOOT POSITION" DATA CALCULATED FROM FRAME HAVING FRAME NUMBER "10" | "BODY VECTOR" DATA CALCULATED FROM FRAME HAVING FRAME NUMBER "10" | 2 |
| 11 | "HAND AND FOOT POSITION" DATA CALCULATED FROM FRAME HAVING FRAME NUMBER "11" | "BODY VECTOR" DATA CALCULATED FROM FRAME HAVING FRAME NUMBER "11" | 2 |
| 12 | "HAND AND FOOT POSITION" DATA CALCULATED FROM FRAME HAVING FRAME NUMBER "12" | "BODY VECTOR" DATA CALCULATED FROM FRAME HAVING FRAME NUMBER "12" | 2 |
| ... | | | |

| BASIC MOTION TYPE | TURN | TURN | TURN | TURN | TURN | ... | TURN FRONT SURFACE MOVEMENT | TURN REAR SURFACE MOVEMENT | ... | DOWNWARD REVERSE 1/4 CONVERSION | UPWARD FORWARD 1/4 CONVERSION |
|---|---|---|---|---|---|---|---|---|---|---|---|
| STARTING POINT BODY ANGLE REGION | 0(180) | 0(180) | 0(180) | 0(180) | 90(270) | ... | 0(180) | 0(180) | ... | 180(0) | 90(270) |
| END POINT BODY ANGLE REGION | 0(180) | 0(180) | 0(180) | 0(180) | 90(270) | ... | 0(180) | 0(180) | ... | 90(270) | 0(180) |
| STARTING POINT LEFT HAND SUPPORT POSITION | 4(2) | 2(4) | 3 | 5(1) | 3 | ... | 2(4) | 4(2) | ... | 2(4) | 4(2) |
| STARTING POINT RIGHT HAND SUPPORT POSITION | 2(4) | 2(4) | 3 | 1(5) | 3 | ... | 4(2) | 4(2) | ... | 4(2) | 4(2) |
| END POINT LEFT HAND SUPPORT POSITION | 4(2) | 2(4) | 3 | 5(1) | 3 | ... | 4(2) | 4(5) | ... | 4(2) | 4(2) |
| END POINT RIGHT HAND SUPPORT POSITION | 2(4) | 2(4) | 3 | 1(5) | 3 | ... | 4(2) | 5(4) | ... | 4(2) | 2(4) |
| PREVIOUS BASIC MOTION TYPE | any | any | any | any | any | ... | TURN REAR SURFACE MOVEMENT | TURN FRONT SURFACE MOVEMENT | ... | any | DOWNWARD REVERSE 1/4 CONVERSION |
| SKILL NAME | HORIZONTAL TURN | ONE HANDLE UPWARD HORIZONTAL TURN | POMMEL HORSE REARWARD HORIZONTAL TURN | HORIZONTAL TURN SANDWICHING BOTH HANDLES | POMMEL HORSE REARWARD VERTICAL TURN | ... | FRONT SURFACE HORIZONTAL MOVEMENT | FRONT SURFACE HORIZONTAL MOVEMENT | ... | EQUAL TO OR LESS THAN DIFFICULTY LEVEL | HANDLE UP-DOWN TURN |
| GROUP | II | II | II | II | II | ... | III | III | ... | | IV |
| DIFFICULTY LEVEL | A | B | B | B | B | ... | A | A | ... | | B |

FIG. 11

| SKILL NAME | | FRONT SCISSOR | REVERSE SCISSOR | HORIZONTAL TURN | ... |
|---|---|---|---|---|---|
| | BODY ROTATION ANGLE | >360 | >360 | >360 | ... |
| | STARTING POINT LEFT HAND SUPPORT POSITION | 3 | 3 | 3 | ... |
| | STARTING POINT RIGHT HAND SUPPORT POSITION | 3 | 3 | 3 | ... |
| | END POINT LEFT HAND SUPPORT POSITION | 3 | 3 | 3 | ... |
| | END POINT RIGHT HAND SUPPORT POSITION | 3 | 3 | 3 | ... |
| PREVIOUS MOTION | PREVIOUS BASIC MOTION TYPE | HANDSTAND TWIST | HANDSTAND TWIST | HANDSTAND TWIST | ... |
| | DIFFICULTY LEVEL UPGRADE NUMBER | 1 | 1 | 2 | ... |

| FRAME NUMBER | RIGHT HAND POSITION | LEFT HAND POSITION | BODY ANGLE | FOOT HEIGHT | BODY ORIENTATION | ... | SEGMENT FLAG | BASIC MOTION TYPE | SKILL NAME | DIFFICULTY LEVEL | E SCORE |
|---|---|---|---|---|---|---|---|---|---|---|---|
| ... | ... | ... | ... | ... | ... | ... | ... | ... | ... | ... | ... |
| 2001 | 2 | 0 | -10 | -0.5 | DOWN | ... | 0 | | | | |
| 2002 | 2 | 4 | 0 | -0.6 | DOWN | ... | 1 | CW FOOT REMOVING | NOT DEFINED | 0 | 0.1 |
| ... | ... | ... | ... | ... | ... | ... | ... | ... | ... | ... | ... |
| 2050 | 2 | 0 | 86 | 0.2 | DOWN | ... | 0 | | | | |
| ... | ... | ... | ... | ... | ... | ... | ... | ... | ... | ... | ... |
| 2362 | 2 | 4 | -20 | -0.6 | DOWN | ... | 1 | CW TURN | HORIZONTAL TURN | A | 0.5 |
| ... | ... | ... | ... | ... | ... | ... | ... | ... | ... | ... | ... |

MOTION RECOGNITION DEVICE AND MOTION RECOGNITION METHOD

CROSS-REFERENCE TO RELATED APPLICATION

This application is a continuation application of International Application PCT/JP2017/036797 filed on Oct. 11, 2017 and designated the U.S., the entire contents of which are incorporated herein by reference. The International Application PCT/JP2017/036797 is based upon and claims the benefit of priority of the prior International Application PCT/JP2016/080150 filed on Oct. 11, 2016, the entire contents of which are incorporated herein by reference.

FIELD

The embodiments discussed herein are related to a motion recognition device and a recognition method.

BACKGROUND

In the field of various types of sports, many efforts or reforms have been carried out for many years in order to evaluate the performances of athletes fairly and accurately. However, recent skill progress of competition is remarkable, and in some cases, it is difficult to make an accurate evaluation simply by the visual observation of the judges. Therefore, a technique for automatically evaluating the performances of the athletes is desired. Hereinafter, one example of the technique for automatically evaluating the performances of the athletes will be described.

A technique, for evaluating the athletes who perform on the horizontal bar, detects keyboards from a two-dimensional silhouette image, recognizes the skill from a combination of keyboards, and performs automatic scoring. However, in the technique, since the skill is recognized using the two-dimensional silhouette image, it is possible to distinguish only a part of the skill of the competition which may be identified only by the two-dimensional silhouette.

Another technique is available to solve the problems. The another technique is a technique for generating a prototype of a movement of a skeleton of an athlete for each skill in advance and comparing each generated prototype with skeleton information of the athlete who conducts the performance to determine the skill.

However, with the above-described techniques, there is a problem that it is not possible to efficiently evaluate performance of a subject.

For example, in the another technique, the skill is identified by using each prototype prepared for each skill. Therefore, in order to distinguish various types of skills, the number of prototypes to be compared increases, and it takes time to recognize the corresponding skill.

The followings are reference documents.
[Document 1] International Publication Pamphlet No. WO2012/12402,
[Document 2] Takuya Yoshimura, Tsuyoshi Hashimoto "A study of improve gesture recognition accuracy using machine learning", Game Programming Workshop 2012, Collection of Papers, pp. 167 to 170, 2012.6 (2012), and
[Document 3] J. Shin and Ozawa, "A Study on Motion Analysis of an Artistic Gymnastics by using Dynamic Image Processing", IEEE International Conference on Systems Man and Cybernetics, pp. 1037 to 1042, 2008.

SUMMARY

According to an aspect of the embodiments, a motion recognition device includes a memory, and a processor coupled to the memory and configured to classify a plurality of frames including positional information of a feature point that corresponds to a predetermined part or a joint part of a body of a subject into a plurality of groups in time series by segmenting the plurality of frames in time series based on a position of the predetermined part of the body of the subject, identify a type of a basic motion that corresponds to the group, based on movement of the feature point included in a consecutive frame, for each group, and evaluate a skill and a difficulty level of a motion performed by the subject based on an order of each type of the basic motion that corresponds to a group which is consecutive in time series.

The object and advantages of the invention will be realized and attained by means of the elements and combinations particularly pointed out in the claims.

It is to be understood that both the foregoing general description and the following detailed description are exemplary and explanatory and are not restrictive of the invention.

BRIEF DESCRIPTION OF DRAWINGS

FIG. 5 is a view illustrating an example of a data structure of calculation result data;
FIG. 8 is a view illustrating an example of a data structure of skill approval rule data;
FIG. 11 is a view illustrating an example of a data structure of upgrade rule data;
FIG. 12 is a view illustrating an example of a data structure of evaluation result data.

DESCRIPTION OF EMBODIMENTS

Hereinafter, examples of a motion recognition device, a motion recognition program, and a motion recognition method disclosed in the present application will be described in detail with reference to the drawings. In addition, the present invention is not limited by the examples.

Example

Figure 1:
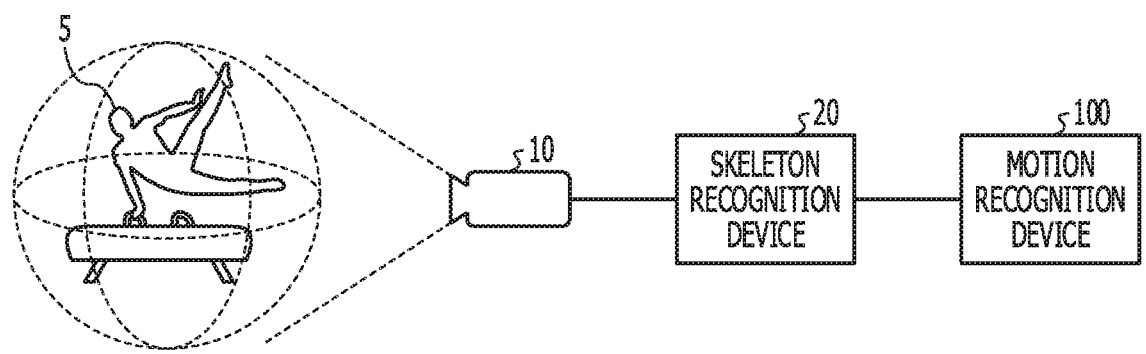
FIG. 1 is a view illustrating a configuration of a system according to the present example.

FIG. 1 is a view illustrating a configuration of a system according to the present example. As illustrated in FIG. 1, the system includes a 3D (dimension) sensor 10, a skeleton recognition device 20, and a motion recognition device 100. For example, a subject 5 performs predetermined gymnastics in an imaging range of the 3D sensor 10. In the present example, as an example, a case where the subject 5 performs on a pommel horse will be described, but the present invention is not limited thereto and may be used in other gymnastics competitions.

The 3D sensor 10 is a sensor that measures distance information from an installation position of the 3D sensor 10 to each observation point on the subject 5 included in the imaging range of the 3D sensor 10. For example, the 3D sensor 10 generates three-dimensional data indicating three-dimensional coordinates of each observation point for each frame, and outputs the generated three-dimensional data to the skeleton recognition device 20. The frame indicates information on the three-dimensional coordinates of each observation point measured by the 3D sensor 10 at a certain timing, and the three-dimensional data is configured with a plurality of frames.

Figure 2:
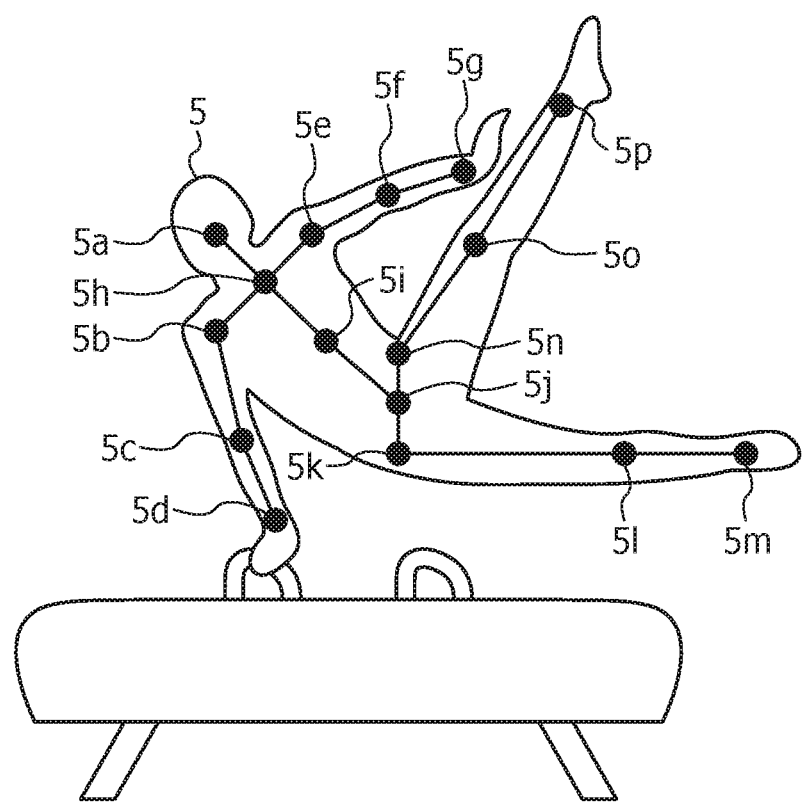
FIG. 2 is a view for describing an example of feature points of a skeleton.

The skeleton recognition device 20 is a device for recognizing a plurality of feature points that configure the skeleton of the subject 5 based on the three-dimensional data. FIG. 2 is a view for describing an example of the feature points of the skeleton. As illustrated in FIG. 2, the feature points of the skeleton include feature points 5a to 5p.

The feature point 5a is a point that corresponds to a position of the head. The feature points 5b and 5e are points that correspond to positions of the shoulder joints (right shoulder joint and left shoulder joint). The feature points 5c and 5f are points that correspond to positions of the elbow joints (right elbow joint and left elbow joint). The feature points 5d and 5g are points that correspond to positions of the wrists (right wrist and left wrist). The feature point 5h is a point that corresponds to a position of the neck. The feature point 5i is a point that corresponds to the back (the center of the back). The feature point 5j is a point that corresponds to the waist (the center of the waist). The feature points 5k and 5n are points that correspond to positions of the crotch joints (right crotch joint and left crotch joint). The feature points 5l and 5o are points that correspond to positions of the knee joints (right knee joint and left knee joint). The feature points 5m and 5p are points that correspond to positions of the ankle (right ankle and left ankle).

Figure 3:
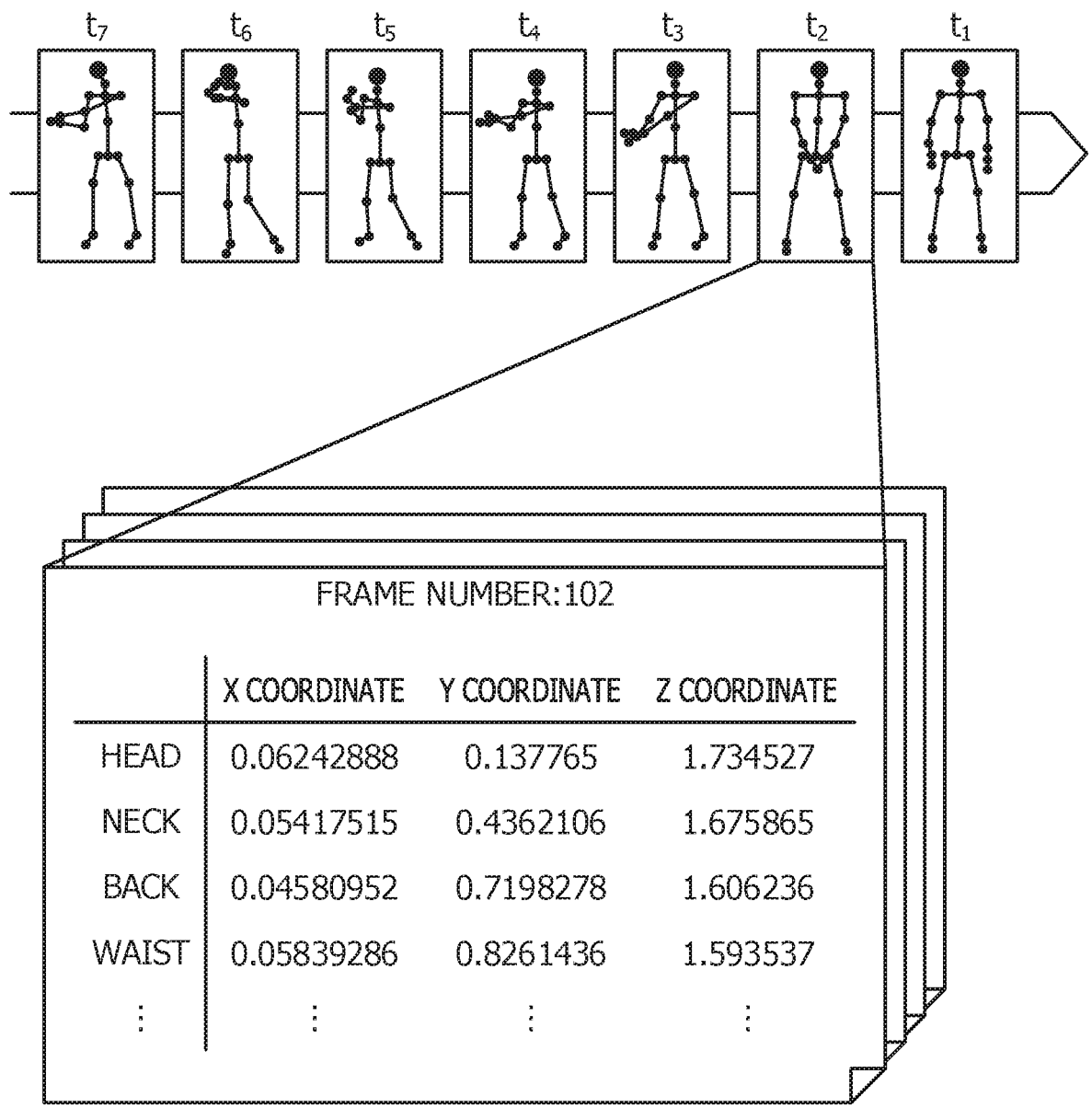
FIG. 3 is a view illustrating an example of a data structure of skeleton data.

Based on the three-dimensional data of each frame, the skeleton recognition device 20 recognizes the feature points of the skeleton for each frame, and generates skeleton data. FIG. 3 is a view illustrating an example of a data structure of the skeleton data. As illustrated in FIG. 3, the skeleton data has three-dimensional coordinates of each of the feature points 5a to 5p for each frame. Each frame is given a frame number that uniquely identifies the frame.

Figure 4:
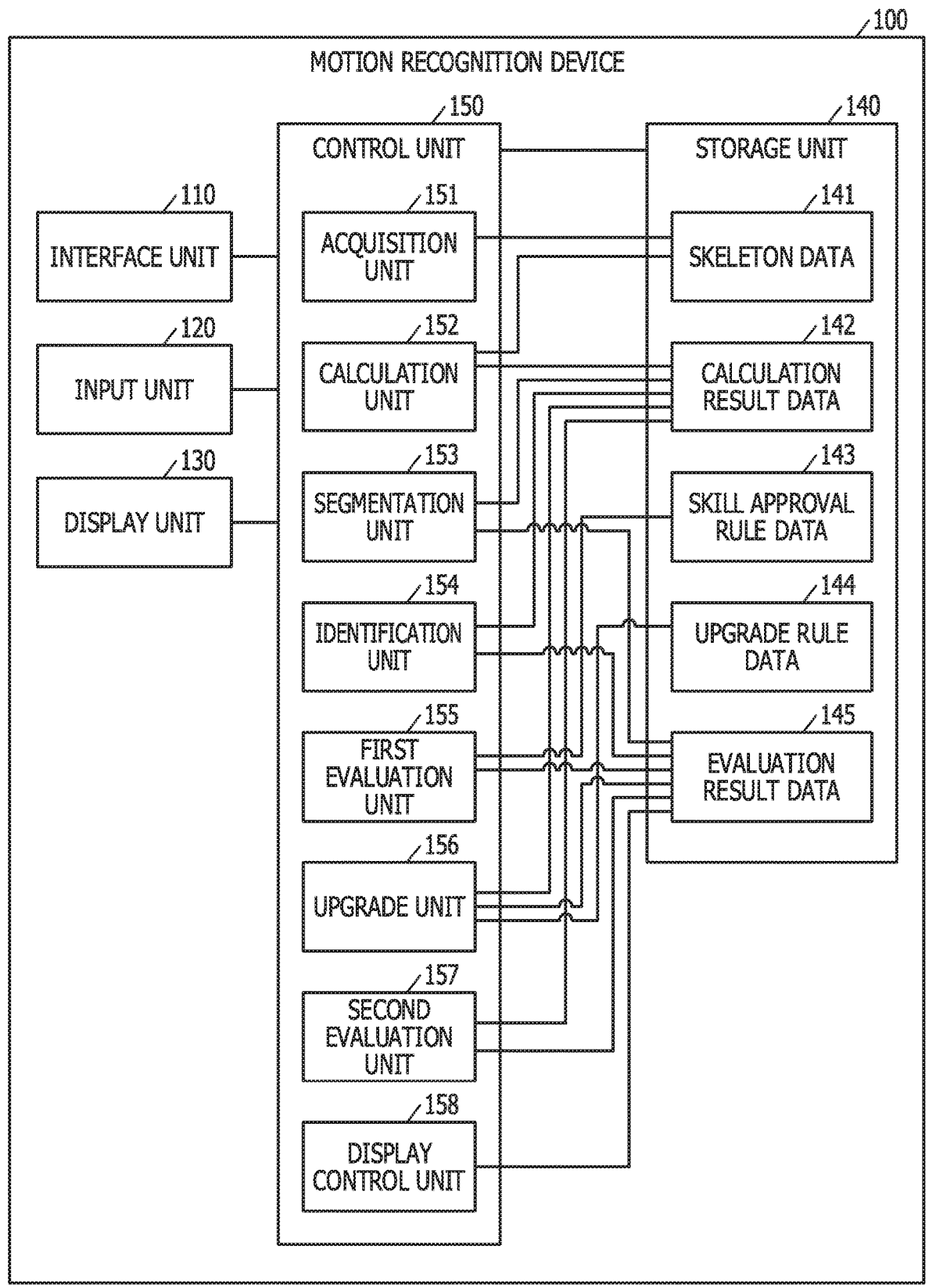
FIG. 4 is a functional block diagram illustrating a configuration of a motion recognition device.

The motion recognition device 100 is a device for evaluating the skill and the difficulty level of the gymnastics performed by the subject 5 based on skeleton data. FIG. 4 is a functional block diagram illustrating a configuration of the motion recognition device. As illustrated in FIG. 4, the motion recognition device 100 includes an interface unit 110, an input unit 120, a storage unit 140, and a control unit 150.

The interface unit 110 is an interface for sending and receiving data to and from the skeleton recognition device 20 or other external devices. The control unit 150 which will be described later exchanges the data with the skeleton identification device 20 via the interface 110.

The input unit 120 is an input device for inputting various types of information to the motion recognition device 100. For example, the input unit 120 corresponds to a keyboard, a mouse, a touch panel, and the like.

The display unit 130 is a display device for displaying information output from the control unit 150. For example, the display unit 130 corresponds to a liquid crystal display, a touch panel, or the like.

The storage unit 140 has skeleton data 141, calculation result data 142, skill approval rule data 143, upgrade rule data 144, and evaluation result data 145. The storage unit 140 corresponds to a semiconductor memory device, such as a random access memory (RAM), a read only memory (ROM), or a flash memory, or a storage device, such as a hard disk drive (HDD).

The skeleton data 141 is skeleton data generated by the skeleton recognition device 20. The data structure of the skeleton data 141 is similar to the data structure of the skeleton data described in FIG. 3.

The calculation result data 142 is data having information on the position and posture of the tip of the hand and foot and the body of the subject 5. The calculation result data 142 is calculated by a calculation unit 152 to be described later. FIG. 5 is a view illustrating an example of a data structure of the calculation result data. As illustrated in FIG. 5, the calculation result data 142 associates the frame number, the hand and foot position data, the body vector data, and the segment number to each other.

Each frame number is information for uniquely identifying the frame. The hand and foot position data is data illustrating three-dimensional coordinates of both hands and both feet. For example, the hand position data corresponds to the three-dimensional coordinates of the feature points 5d and 5g of the wrist. For example, the foot position data corresponds to the three-dimensional coordinates of the feature points 5m and 5p of the ankle. The body vector data is data indicating the direction and magnitude of the body vector.

Figure 6:
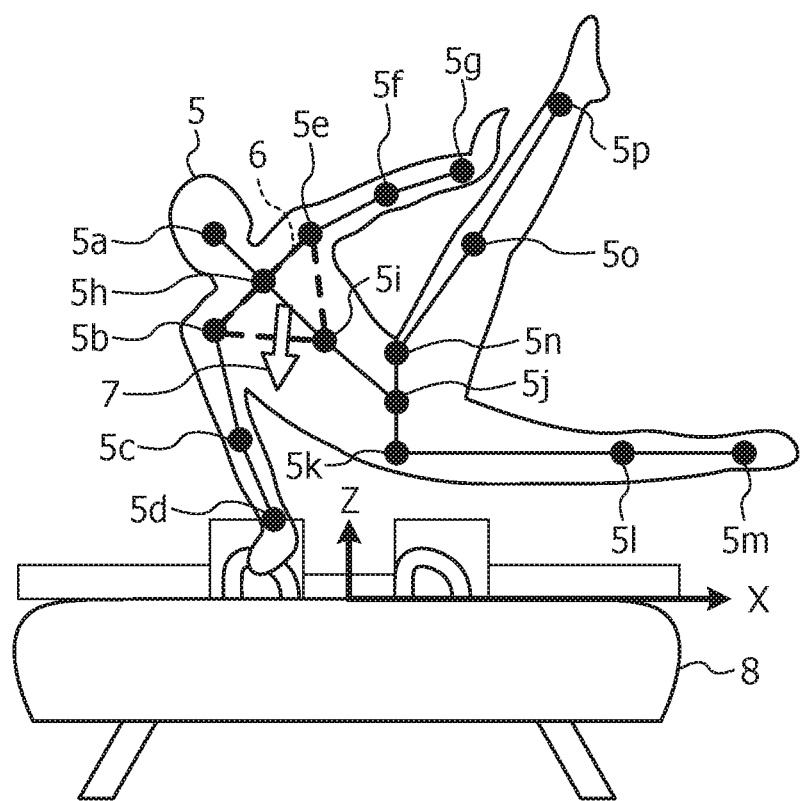
FIG. 6 is a view for describing an example of a body vector.

FIG. 6 is a view for describing an example of the body vector. As illustrated in FIG. 6, the body vector 7 corresponds to the normal vector of a plane 6 that passes through the feature point 5b of the right shoulder joint, the feature point 5e of the left shoulder joint, and the feature point 5i of the back. For example, the magnitude of the body vector 7 is set to "1". For example, the body vector is defined by an orthogonal coordinate system configured with an X axis, a Y axis, and a Z axis. A direction of the X axis is set to a longitudinal direction of a pommel horse 8. A direction of the Y axis is set to a direction orthogonal to the X axis. A direction of the Z axis is set to a vertically upward direction of an XY plane. In addition, when the body vector 7 is obtained, an angle between the pommel horse and the body may be defined.

Figure 7:
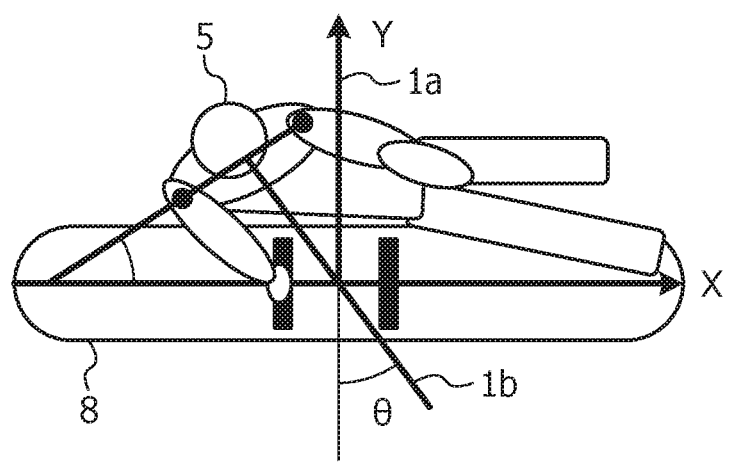
FIG. 7 is a view for describing an angle between a pommel horse and a body.

The angle between the pommel horse and the body will be described. FIG. 7 is a view for describing the angle between the pommel horse and the body. As illustrated in FIG. 7, an angle θ between the pommel horse and the body is an angle between a line segment 1*a* and a line segment 1*b*. The line segment 1*b* is a line segment obtained by making the body vector 7 projected onto the XY plane extend to the front of the subject 5. The line segment 1*a* is a line segment that corresponds to the Y axis.

The segment number is a number that indicates to which group the frame belongs. The group treats each frame from a frame which is a starting point of a basic motion to a frame which is an end point of the basic motion as a set in a case where the subject performs a certain basic motion.

The same segment number is assigned to frames belonging to the same group. The segment number is set by a segmentation unit 153 which will be described later. For example, in a plurality of frames which are consecutive in time series, the plurality of frames included in frames from a frame that serves as a segment point to a frame that serves as the next segment point are frames included in the same group. In the following description, the plurality of frames belonging to the same group are appropriately described as "partial data". An identification unit 154 which will be described later specifies the type of the basic motion that corresponds to the partial data for each piece of partial data.

The description will be made returning to FIG. 4. The skill approval rule data 143 is data used in a case where a first evaluation unit 155 which will be described later determines the skill name and the difficulty level. FIG. 8 is a view illustrating an example of a data structure of the skill approval rule data. As illustrated in FIG. 8, the skill approval rule data 143 includes basic motion type, starting point body angle region, end point body angle region, starting point left hand support position, starting point right hand support position, end point left hand support position, end point right hand support position, previous basic motion type, skill name, group, and difficulty level.

The basic motion type indicates the type of the basic motion. The starting point body angle region indicates in which predetermined angle region the direction of the body vector is included in the frame at the starting point included in the partial data. The end point body angle region indicates in which predetermined angle region the direction of the body vector is included in the frame at the end point included in the partial data. In the starting point body angle region and the end point body angle region of FIG. 8, A(B) indicates that the angle region may be a region A or may be a region B in combination of the outer part of ( ) or the inner part of ( ).

Figure 9:
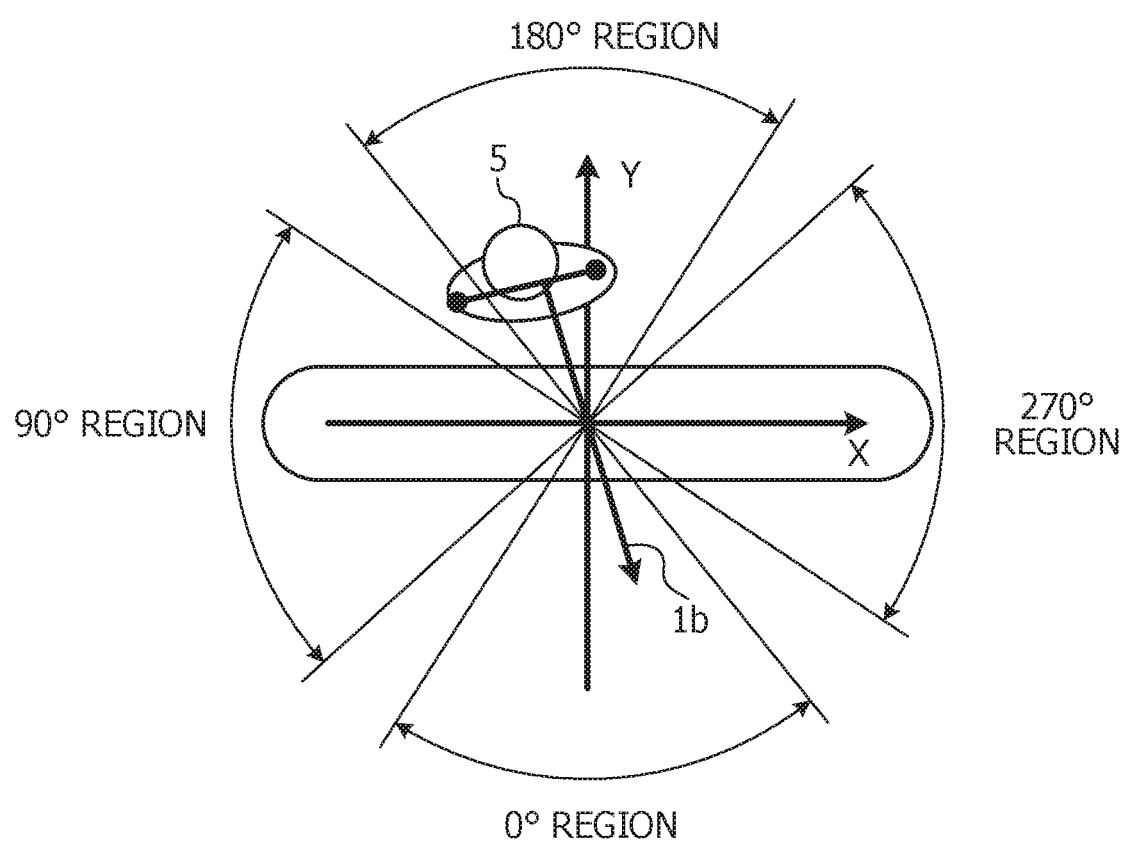
FIG. 9 is a view illustrating an example of an angle region.

FIG. 9 is a view illustrating an example of the angle region. As illustrated in FIG. 9, the angle region includes a 0° region, a 90° region, a 180° region, and a 270° region. The line segment 1*b* is a line segment obtained by making the body vector 7 of the subject 5 projected onto the XY plane extend to the front of the subject 5. In the example illustrated in FIG. 9, the direction of the body vector 7 is the 0° region.

The starting point left hand support position indicates to which predetermined support position on the pommel horse the position of the left hand (left wrist) of the subject 5 corresponds, in the frame at the starting point included in the partial data. The starting point right hand support position indicates to which predetermined support position on the pommel horse the position of the right hand (right wrist) of the subject 5 corresponds. In the starting point left hand support position and the starting point right hand support position of FIG. 8, A(B) indicates that the support position may be a region A or may be a support position B in combination of the outer part of ( ) or the inner part of ( ).

The end point left hand support position indicates to which predetermined support position on the pommel horse the position of the left hand (left wrist) of the subject 5 corresponds, in the frame at the end point included in the partial data. The end point right hand support position indicates to which predetermined support position on the pommel horse the position of the right hand (right wrist) of the subject 5 corresponds, in the frame at the end point included in the partial data. In the end point left hand support position and the end point right hand support position of FIG. 8, A(B) indicates that the support position may be a support position A or may be a support position B in combination of the outer part of ( ) or the inner part of ( ).

Figure 10:
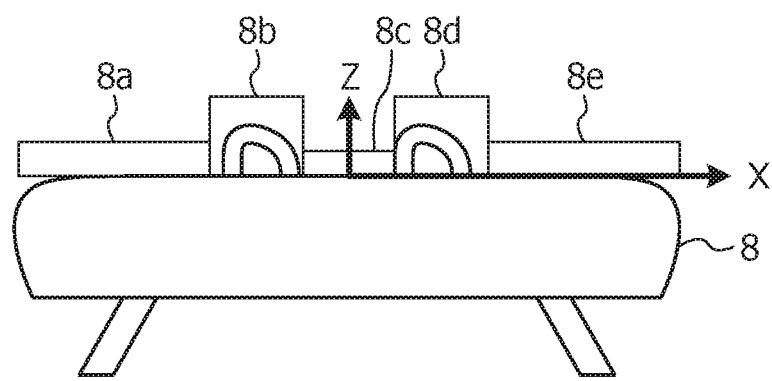
FIG. 10 is a view illustrating an example of a support position.

FIG. 10 is a view illustrating an example of the support position. In a case where the hand (left hand or right hand) of the subject 5 exists in the region 8*a*, the position of the hand corresponds to the support position "1". In a case where the hand of the subject 5 exists in the region 8*b*, the position of the hand corresponds to the support position "2". In a case where the hand of the subject 5 exists in the region 8*c*, the position of the hand corresponds to the support position "3". In a case where the hand of the subject 5 exists in the region 8*d*, the position of the hand corresponds to the support position "4". In a case where the hand of the subject 5 exists in the region 8*e*, the position of the hand corresponds to the support position "5".

The previous basic motion type indicates the type of the basic motion that corresponds to the partial data one piece earlier in time series than the partial data of interest. A previous basic motion type "any" indicates that the type of the previous basic motion may be any type. In the following description, the partial data one piece earlier in time series than the partial data of interest is expressed as "previous partial data".

The skill name is the name of skill specified by the basic motion type, the starting point body angle region, the end point body angle region, the starting point left hand support position, the starting point right hand support position, the end point left hand support position, the end point right hand support position, and the previous basic motion type.

The group indicates a group in which the skill specified by the skill name is classified. The difficulty level indicates the difficulty level of the skill. The difficulty level of the skill is higher in the order of A, B, C, D, and E. The difficulty level A has the lowest difficulty level.

The description will be made returning to FIG. 4. The upgrade rule data 144 is data used in a case where an upgrade unit 156 which will be described later determines whether to upgrade the difficulty level of the skill. FIG. 11 is a view illustrating an example of a data structure of the upgrade rule data. As illustrated in FIG. 11, the upgrade rule data 144 includes the skill name, the body rotation angle in the previous motion, the starting point left hand support position in the previous motion, the starting point right hand support position in the previous motion, the end point left hand support position in the previous motion, and the end point right hand support position in the previous motion. In addition, the upgrade rule data 144 has a previous basic motion type and a difficulty level upgrade number.

In FIG. 11, the skill name corresponds to the skill name specified by the first evaluation unit 155 for the partial data of interest and is a target of whether to upgrade the difficulty level. The body rotation angle in the previous motion indicates the sum of the rotation angles of the body vector from the frame at the starting point to the frame at the end point included in the previous partial data. For example, as described in FIG. 9, the rotation angle is the rotation angle in a case where the body vector is projected onto the XY plane. The sum of the rotation angles is calculated assuming that the position of the body vector of the frame which is the starting point of the previous partial data is projected onto the XY plane, as 0°.

The starting point left hand support position in the previous motion indicates to which predetermined support position on the pommel horse the position of the left hand (left wrist) of the subject 5 corresponds, in the frame at the starting point included in the previous partial data. The starting point right hand support position in the previous motion indicates to which predetermined support position on the pommel horse the position of the right hand (right wrist) of the subject 5 corresponds, in the frame at the starting point included in the previous partial data.

The end point left hand support position in the previous motion indicates to which predetermined support position on the pommel horse the position of the left hand (left wrist) of the subject 5 corresponds, in the frame at the end point included in the previous partial data. The end point right hand support position in the previous motion indicates to which predetermined support position on the pommel horse the position of the right hand (right wrist) of the subject 5 corresponds, in the frame at the end point included in the previous partial data.

The basic motion type indicates the type of the basic motion that corresponds to the previous partial data.

The difficulty level upgrade number is information indicating how many levels the difficulty level of the skill specified by the first evaluation unit 155 is upgraded in a case where the corresponding condition is hit. For example, the skill name specified by the first evaluation unit 155 is "Front Scissor", the body rotation angle is "less than 360°", the starting point and the end point and each support position of the left hand and the right hand in the previous motion are "3", and the previous basic motion type is "Handstand Twist". In this case, the record in the first column of the upgrade rule data 144 is hit, and the difficulty level upgrade number becomes "1". For example, in a case where the current difficulty level is "A", when the difficulty level is upgraded one step higher, the corrected difficulty level becomes "B".

The evaluation result data 145 is data that holds information on the evaluation result of the performance of the subject 5. FIG. 12 is a view illustrating an example of a data structure of the evaluation result data. As illustrated in FIG. 12, the evaluation result data 145 associates frame number, right hand position, left hand position, body angle, foot height, body orientation, segment flag, basic motion type, skill name, difficulty level, and E score to each other.

Each frame number is information for uniquely identifying the frame. The right hand position indicates to which predetermined support position on the pommel horse the position of the right hand (right wrist) of the subject 5 corresponds. The left hand position indicates to which predetermined support position on the pommel horse the position of the left hand (left wrist) of the subject 5 corresponds.

The body angle indicates the body angle of the subject 5. For example, the angle between the line segment in a case of projecting the body vector obtained from the corresponding frame onto the XY plane and the Y axis is defined as the body angle. The foot height indicates a higher position of the position of the right foot (right ankle) of the subject 5 and the left foot (left ankle) position of the subject.

The body orientation indicates whether the direction of the Z axis of the body vector is a positive direction or a negative direction. "Down" of the body orientation indicates that the orientation of the Z axis of the body vector is negative. "Up" of the body orientation indicates that the orientation of the Z axis of the body vector is positive.

The segment flag is information indicating whether or not the corresponding frame corresponds to the segment point. Whether or not the corresponding frame is a segment point is determined by the segmentation unit 153 which will be described later. In a case where the corresponding frame is a segment point, the segment flag is set to "1". In a case where the corresponding frame is not a segment point, the segment flag is set to "0".

The description related to the basic motion type, the skill name, and the difficulty level is the same as the description related to the basic motion type, the skill name, and the difficulty level described in FIG. 8.

The execution score (E score) indicates an E score of the basic motion type that corresponds to the partial data. The E score is calculated by a second evaluation unit 157 which will be described later.

The description will be made returning to FIG. 4. The control unit 150 includes an acquisition unit 151, the calculation unit 152, the segmentation unit 153, the identification unit 154, the first evaluation unit 155, the upgrade unit 156, the second evaluation unit 157, and a display control unit 158. The control unit 150 may be realized by a central processing unit (CPU), a micro processing unit (MPU), or the like. In addition, the control unit 150 may also be realized by a hard wired logic, such as an application specific integrated circuit (ASIC) or a field programmable gate array (FPGA).

The acquisition unit 151 is a process unit that acquires the skeleton data 141 from the skeleton recognition device 20. The acquisition unit 151 registers the acquired skeleton data 141 in the storage unit 140. The data structure of the skeleton data 141 is the data structure described in FIG. 3.

The calculation unit 152 is a process unit that calculates the calculation result data 142 based on the skeleton data 141. The data structure of the calculation result data 142 is the data structure described in FIG. 5. In the calculation result data 142, the hand and foot position data and the body vector data that correspond to the frame number are registered by the calculation unit 152, and the segment number is registered by the segmentation unit 153.

The calculation unit 152 calculates the hand and foot position data and the body vector data for each frame. For example, the calculation unit 152 calculates the three-dimensional coordinates of the feature points 5$d$ and 5$g$ of the skeleton data 141 as the position of the hand. The calculation unit 152 calculates the three-dimensional coordinates of the feature points 5$m$ and 5$p$ of the skeleton data 141 as the position of the foot. The calculation unit 152 registers the hand and foot position data in the calculation result data 142 in association with the frame number of the corresponding frame.

The calculation unit 152 calculates the normal vector of the plane 6 that passes through the feature point 5$b$ of the right shoulder joint, the feature point 5$e$ of the left shoulder joint, and the feature point 5$i$ of the back, as the body vector. The calculation unit 152 registers the body vector data in the calculation result data 142 in association with the frame number of the corresponding frame.

The calculation unit 152 repeatedly executes the above-described process for each frame of the skeleton data 141 to generate the calculation result data 142.

The segmentation unit 153 is a process unit that specifies a frame that serves as a segment point based on the calculation result data 142 and classifies the plurality of frames into the plurality of groups based on the specified segment point. The segmentation unit 153 accesses the calculation result data 142 and sets the segment numbers of the frames belonging to the same group to be the same.

In the calculation result data 142, the segmentation unit 153 refers to the hand and foot position data that corresponds to a certain frame number. In a case where all of the following conditions A1, A2, and A3 are satisfied, the segmentation unit 153 determines that the frame that corresponds to a certain frame number is a segment point. A case where all of the conditions A1 to A3 are satisfied means that the direction of the body vector is downward while both hands of the subject 5 are on the pommel horse 8.

Condition A1: The position of the left hand of the subject 5 is positioned in one of the regions 8a to 8e illustrated in FIG. 10.

Condition A2: The position of the right hand of the subject 5 is positioned in one of the regions 8a to 8e illustrated in FIG. 10.

Condition A3: A Z axis component of the body vector is negative.

The segmentation unit 153 accesses the evaluation result data and sets the segment flag that corresponds to the frame number determined as the segment point to "1". An initial value of the segment flag is set to "0".

Figure 13:
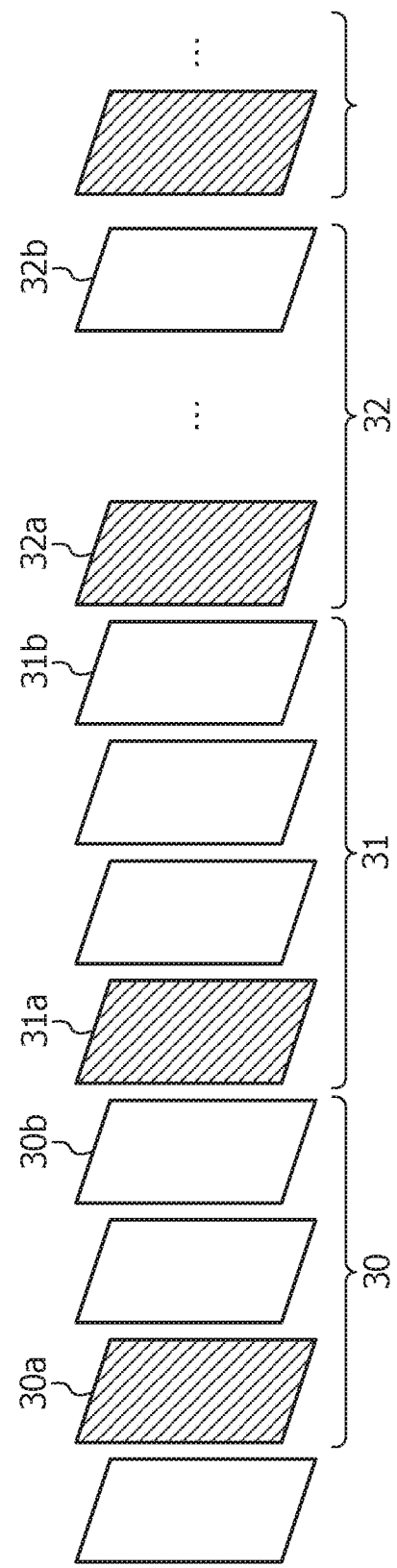
FIG. 13 is a view for describing an example of a process of a segmentation unit.

FIG. 13 is a view for describing an example of the process of the segmentation unit. The plurality of frames illustrated in FIG. 13 are arranged in time series. As an example, it is assumed that the frames 30a, 31a, and 32a satisfy the above-described conditions A1 to A3 and are frames at the segment point. In this case, the segmentation unit 153 classifies each frame included in the range 30 into the same group. The segmentation unit 153 classifies each frame included in the range 31 into the same group. The segmentation unit 153 classifies each frame included in the range 32 into the same group.

The segment number of each frame included in the range 30 is "n", the segment number of each frame included in the range 31 is "n+1", and the segment number of each frame included in the range 32 is "n+2". n is a natural number of 1 or more.

For example, in each frame included in the range 30, the frame 30a at the front is the frame at the starting point, and a frame 30b at the end is the frame at the end point. In each frame included in the range 31, the frame 31a at the front is the frame at the starting point, and a frame 31b at the end is the frame at the end point. In each frame included in the range 32, the frame 32a at the front is the frame at the starting point, and a frame 32b at the end is the frame at the end point.

Here, the "partial data" and the "previous partial data" will be described again. The data in which each frame included in the ranges 30, 31, and 32 is grouped respectively becomes the partial data. Assuming that the partial data of interest is each frame included in the range 31, the previous partial data is each frame included in the range 31.

The identification unit 154 is a process unit for identifying the basic motion type that corresponds to the partial data based on the movement of the feature point of the frame included in the partial data for each piece of the partial data. The identification unit 154 acquires the information of the feature point of the frame included in the partial data from the calculation result data 142. When identifying the basic motion type that corresponds to the partial data, the identification unit 154 registers the identification result in the evaluation result data 145 in association with the frame number.

For example, the identification unit 154 uses Hidden Markov Model (HMM). The HMM is a probability model in which time series data is input and which determines to which category (basic motion type) the time series data belongs. The identification unit 154 includes a learning phase and a recognition phase.

In the learning phase, the HMM obtains four sets of parameter sets λ for each basic motion type. The parameter set λ is defined by Equation (1).

$$\lambda = \{Q, A, B, \pi\} \qquad (1)$$

In Equation (1), Q indicates a set of states and is defined by Equation (2).

$$Q = \{a_1, q_2, \ldots, q_n\} \qquad (2)$$

In Equation (1), A indicates a state transition probability matrix which is a set of transition probabilities $a_{ij}$ from a state $q_i$ to a state $q_j$ and is defined by Equation (3).

$$A = \{a_{ij}\} \qquad (3)$$

In Equation (1), B indicates a set of probability distributions that output a vector x in the state $q_j$. In Equation (1), π indicates a set of initial states and is defined by Equation (4).

$$\pi = \{\pi i\} \qquad (4)$$

Here, a probability density function in the state $q_i$ is defined by Equation (5). In Equation (5), $u_i$ indicates an average vector of the probability density function. $\Sigma_i$ indicates a covariance matrix of the probability density function.

[Formula 1]

$$b_i(x) = \frac{1}{\sqrt{(2\pi)^m |\Sigma_i|}} \exp\left\{\frac{1}{2}(x-\mu_i)^T \sum_i^{-1} (x-\mu_i)\right\} \qquad (5)$$

An example of the process of the learning phase of the identification unit 154 will be described. In a case of determining the parameter set λ of a certain basic motion type, the identification unit 154 randomly sets the covariance parameters of the HMM as an initial state. The identification unit 154 prepares a plurality of pieces of partial data that correspond to a certain basic motion identification and performs process of calculating an HMM likelihood P ($O_{segment}|\Lambda_k$) for the partial data $O_{segment}$.

The identification unit 154 repeatedly executes a process of optimizing the parameter set of $\Lambda_k$ by using the partial data having the maximum likelihood P as a teacher signal of $\Lambda_k$ related to the HMM. By the process, the identification unit 154 specifies the parameter set λ of a certain basic motion type. The identification unit 154 learns the parameter set λ for each basic motion type by performing the same process for the other basic motion types.

An example of the process of the recognition phase of the identification unit 154 will be described. When acquiring the partial data to be recognized for the basic motion type, the identification unit 154 specifies the maximum $\Lambda_{k0}$ of $\Lambda_k$ for each parameter set λ while changing the parameter set learned in the learning phase based on Equation (6). The identification unit 154 determines the basic motion type that corresponds to the parameter set λ used when calculating $\Lambda_{k0}$ as the basic motion type of the partial data to be recognized.

[Formula 2]

$$\Lambda_{k0} = \underset{\Lambda_k}{\mathrm{argmax}}\, P(O_{segment} | \Lambda_k) \qquad (6)$$

The first evaluation unit 155 is a process unit that evaluates the skill and the difficulty level of the motion performed by the subject 5 based on the order of the basic motion types that correspond to the partial data which is consecutive in time series. Hereinafter, an example of the process of the first evaluation unit 155 will be described. Here, the partial data to be evaluated is simply expressed as the partial data, and the partial data one piece earlier than the partial data to be evaluated is expressed as the previous partial data.

The first evaluation unit 155 specifies the basic motion type of the partial data based on the frame number included in the partial data and the evaluation result data 145. The first evaluation unit 155 specifies the previous basic motion type of the previous partial data based on the frame number included in the previous partial data and the evaluation result data 145.

Using the frame number of the frame at the starting point included in the partial data as a key, the first evaluation unit 155 refers to the calculation result data 142 and specifies the starting point body angle region, the starting point left hand support position, and the starting point right hand support position. Using the frame number of the frame at the end point included in the partial data as a key, the first evaluation unit 155 refers to the calculation result data 142 and specifies the end point body angle region, the end point left hand support position, and the end point right hand support position.

For example, the first evaluation unit 155 specifies the starting point body angle region and the end point body angle region by comparing the definition of each angle region described in FIG. 9 with the body vector. The first evaluation unit 155 specifies the starting point left hand support position, the starting point right hand support position, the end point left hand support position, and the end point right hand support position by comparing each of the regions 8a to 8e described in FIG. 10 with the position data of the hand.

The first evaluation unit 155 identifies the skill name, the difficulty level, and the group that correspond to the partial data by comparing each piece of the specified information with the skill approval rule data 143. Here, each piece of the specified information includes the basic motion type and the previous motion type. In addition, each piece of the specified information includes the starting point body angle region, the starting point left hand support position, the starting point right hand support position, the end point body angle region, the end point left hand support position, and the end point right hand support position.

The first evaluation unit 155 registers the specified skill name, difficulty level, and group in the evaluation result data 145 in association with the frame number of the frame included in the partial data. In addition, the first evaluation unit 155 registers the right hand position, the left hand position, the body angle, the foot height, and the body orientation in association with the frame number. The first evaluation unit 155 specifies the skill name, the difficulty level, and the group by repeatedly executing the above-described process for the other pieces of partial data and registers the skill name, the difficulty level, and the group in the evaluation result data 145.

The upgrade unit 156 is a process unit that determines whether to upgrade the difficulty level evaluated by the first evaluation unit 155, and upgrades the difficulty level based on the determination result. Hereinafter, an example of the process of the upgrade unit 156 will be described. Here, the partial data to be evaluated is simply expressed as the partial data, and the partial data one piece earlier than the partial data to be evaluated is expressed as the previous partial data.

The upgrade unit 156 refers to the evaluation result data 145 by using the frame number of the frame included in the partial data as a key and specifies the skill name that corresponds to the partial data evaluated by the first evaluation unit 155.

The upgrade unit 156 calculates the body rotation angle based on the body vector of each frame included in the partial data. The body rotation angle is the sum of changes in body angle from the frame at the starting point to the frame at the end point. The upgrade unit 156 acquires the data of the body vector of each frame from the calculation result data 142.

Using the frame number of the frame at the starting point included in the partial data as a key, the upgrade unit 156 refers to the calculation result data 142 and specifies the starting point left hand support position and the starting point right hand support position. Using the frame number of the frame at the end point included in the partial data as a key, the upgrade unit 156 refers to the calculation result data 142 and specifies the end point left hand support position and the end point right hand support position. The upgrade unit 156 specifies the previous basic motion type of the previous partial data based on the frame number included in the previous partial data and the evaluation result data 145.

The upgrade unit 156 determines whether to upgrade the difficulty level that corresponds to the partial data by comparing each piece of the specified information with the upgrade rule data 144. Here, each piece of the specified information includes the skill name, the body rotation angle, the starting point left hand support position, the starting point right hand support position, the end point left hand support position, the end point right hand support position, and the previous basic motion type.

The upgrade unit 156 determines that the difficulty level is upgraded in a case where a column record that hits each piece of the specified information exists in the upgrade rule data 144. The upgrade unit 156 determines that the difficulty level is not upgraded in a case where the column record that hits each piece of the specified information does not exist in the upgrade rule data 144. In order to determine how many stages to upgrade, the difficulty level upgrade number of the hit column record is referred to.

For example, the skill name of the partial data is "Front Scissor", the body rotation angle is "less than 360°", the starting point and the end point and each support position of the left hand and the right hand in the previous motion are "3", and the previous basic motion type is "Handstand Twist". In this case, the record in the first column of the upgrade rule data 144 is hit, and the difficulty level upgrade number becomes "1". In addition, in a case where the current difficulty level of the partial data is "A", the upgrade unit 156 corrects the difficulty level to "B".

The upgrade unit 156 updates the difficulty level of the evaluation result data 145 by repeatedly executing the above-described process with respect to the other pieces of partial data.

The second evaluation unit 157 is a process unit that evaluates the E score of the basic motion for each piece of partial data. In the second evaluation unit 157, it is assumed that a policy for calculating the E score is previously set for each basic motion type. Here, as an example, an example in which the second evaluation unit 157 calculates the E score of the basic motion type "Down" will be described. "Down" here indicates the basic motion when the subject 5 goes down from the pommel horse.

The second evaluation unit 157 uses an evaluation function F(k) illustrated in Equation (7). The evaluation function F(k) is a function for evaluating the k-th frame among the plurality of frames included in the partial data to be evaluated.

$$F(k)=\arcsin(Tz/Tx) \quad (7)$$

Figure 14:
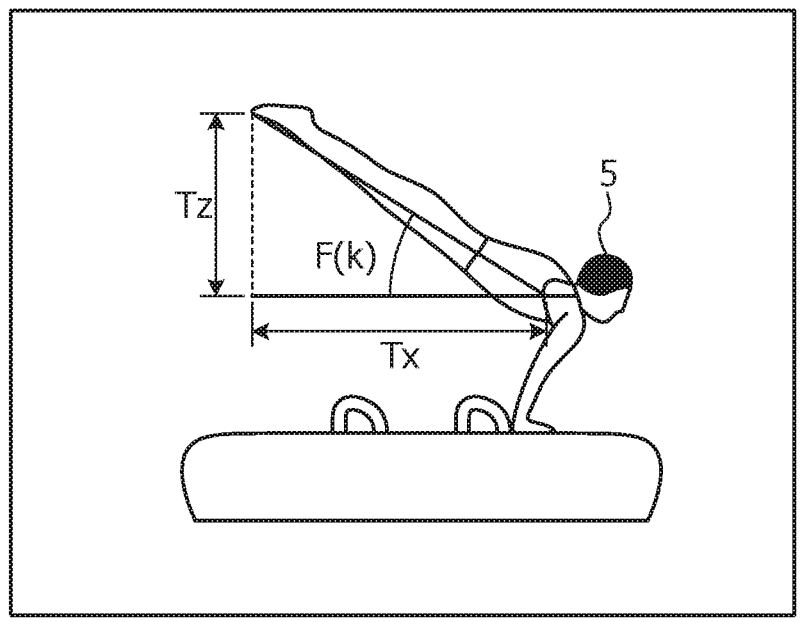
FIG. 14 is a view for describing an evaluation function F(k)

FIG. 14 is a view for describing the evaluation function F(k). In FIG. 14, Tx corresponds to the length of the X component from the shoulder joint to the tip of the toe (ankle) of the subject 5 in the k-th frame. Tz corresponds to the length of the Z component from the shoulder joint to the tip of the toe of the subject 5 in the k-th frame. For example, the position of the shoulder joint corresponds to the position of feature point 5b or 5e. The tip of the toe corresponds to the position of the feature point 5m or 5p.

In a case of evaluating "Down", the second evaluation unit 157 repeatedly executes the above-described process for each frame included in the target partial data and calculates the value of F(k) for each frame. The second evaluation unit 157 does not determine the defect "0.3" on each frame which the value of F(k) is greater than 30°. The second evaluation unit 157 determines the defect "0.3" for the basic emotion, in a case where a frame in which the value of F(k) is greater than 30° appears.

The second evaluation unit 157 calculates the final E score for the basic motion based on Equation (8). Σ illustrated in Equation (8) indicates the sum of defects determined by the result of the evaluation function in all pieces of the partial data. In addition, in the description above, the "Down" evaluation function has been described as an example, but for other basic motions, the defects are also determined by the evaluation function that corresponds to the corresponding basic motion. For example, the evaluation function of the partial data of "Turn" is an evaluation function for evaluating the alignment of the tips of the left and right feet, and as much as both the left and right feet are not aligned, the defect becomes larger.

$$E\text{score}=10-\Sigma \quad (8)$$

The second evaluation unit 157 registers the information of the calculated E score in the evaluation result data 145 in association with the frame number. The second evaluation unit 157 may register the E score in the record of each frame included in the same partial data or may register the E score in the record of the frame at the starting point among the frames included in the same partial data. The second evaluation unit 157 similarly calculates the E score for the other pieces of partial data and registers the E score in the evaluation result data 145.

In addition, the first evaluation unit 155 may re-determine the difficulty level of the skill by using the evaluation result data 145 and a logical expression indicating a rule. The logical expression indicating a rule is a logical expression that associates the order of the skill name of each basic motion with a difficulty score (D score).

Figure 15:
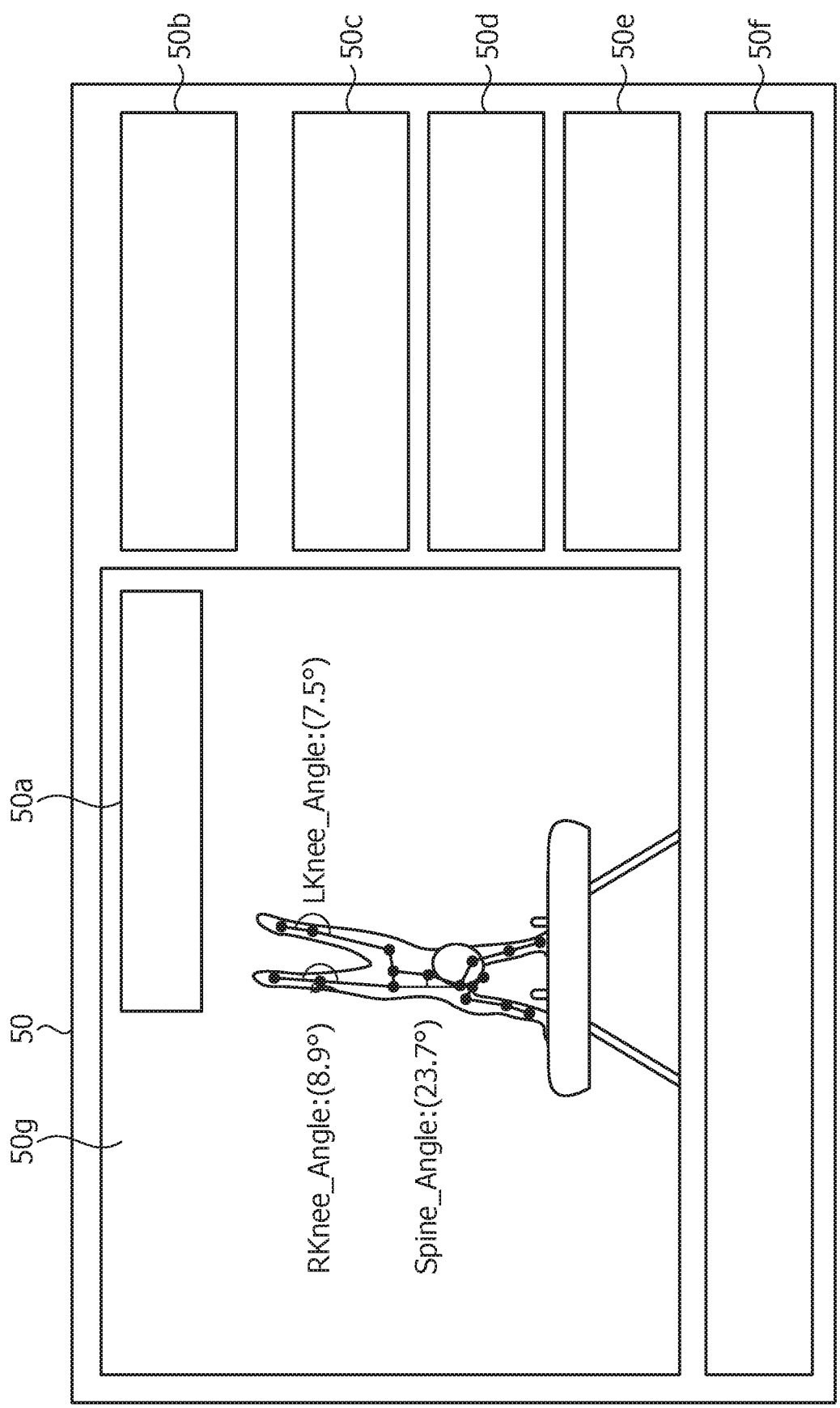
FIG. 15 is a view illustrating an example of a display screen.

The display control unit 158 is a process unit that generates a display screen based on the evaluation result data 145 and displays the display screen on the display unit 130. FIG. 15 is a view illustrating an example of the display screen. As illustrated in FIG. 15, a display screen 50 includes regions 50a to 50g. In addition, the display control unit 158 may display the evaluation result data 145 on the display unit 130 as it is.

The region 50a is a region that displays the hand and foot position data and the body vector data of the current subject 5. The region 50b is a region that displays the hand and foot position data and the body vector data when the subject 5 starts the performance. The region 50c is a region that displays the hand and foot position data and the body vector data of the current subject 5 specified by the frame one piece earlier than the current frame. The region 50d is a region that displays the hand and foot position data and the body vector data of the current subject 5 specified by the frame two pieces earlier than the current frame. The region 50e is a region that displays the hand and foot position data and the body vector data of the current subject 5 specified by the frame three pieces earlier than the current frame. The region 50f is a region that displays the skill name of the basic motion specified by the partial data including the current frame. The region 50g is a region that displays an image visualizing the information of the 3D sensor 10.

Figure 16:
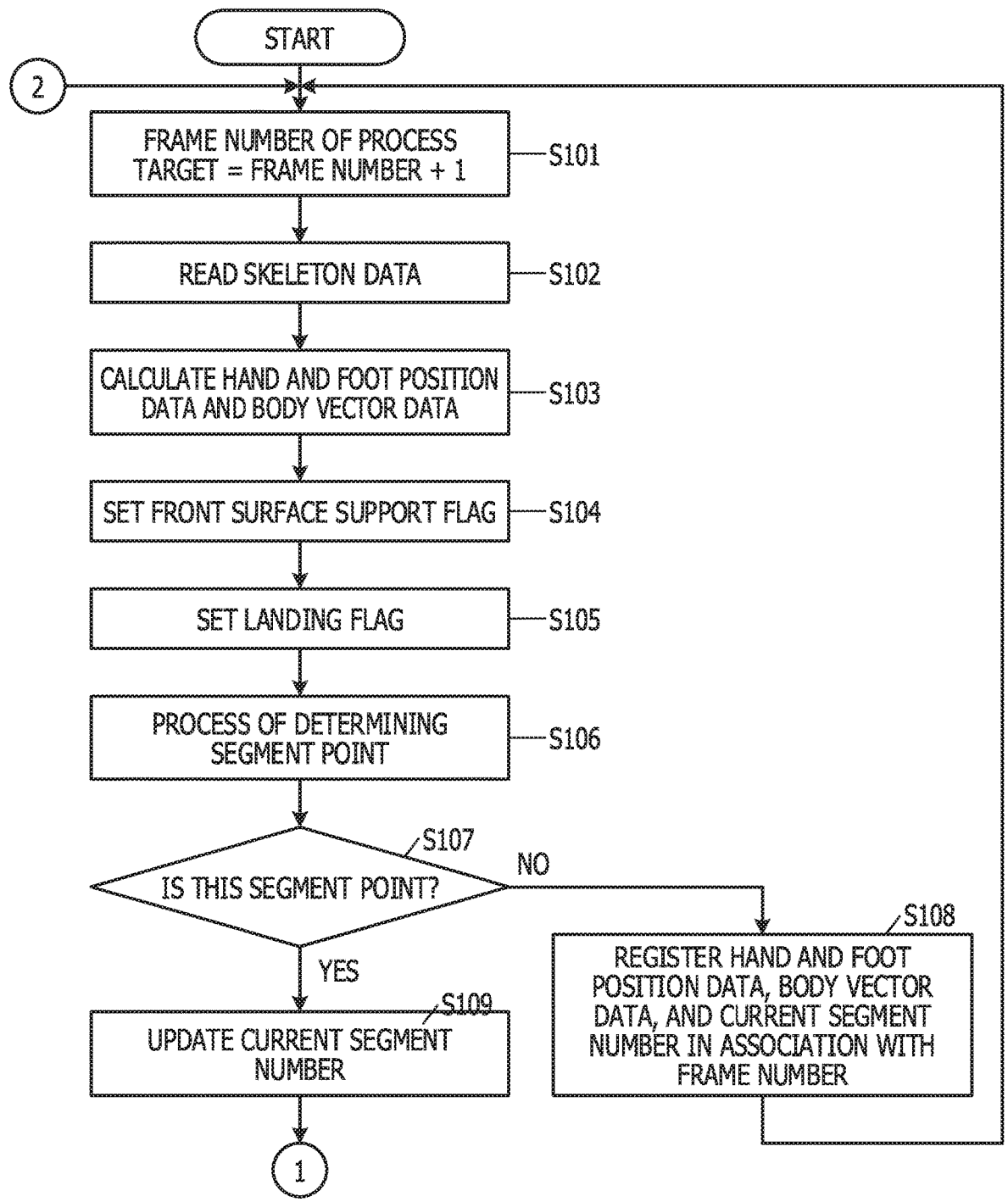
FIG. 16 is a flowchart (1) illustrating a process procedure of the motion recognition device.
Figure 17:
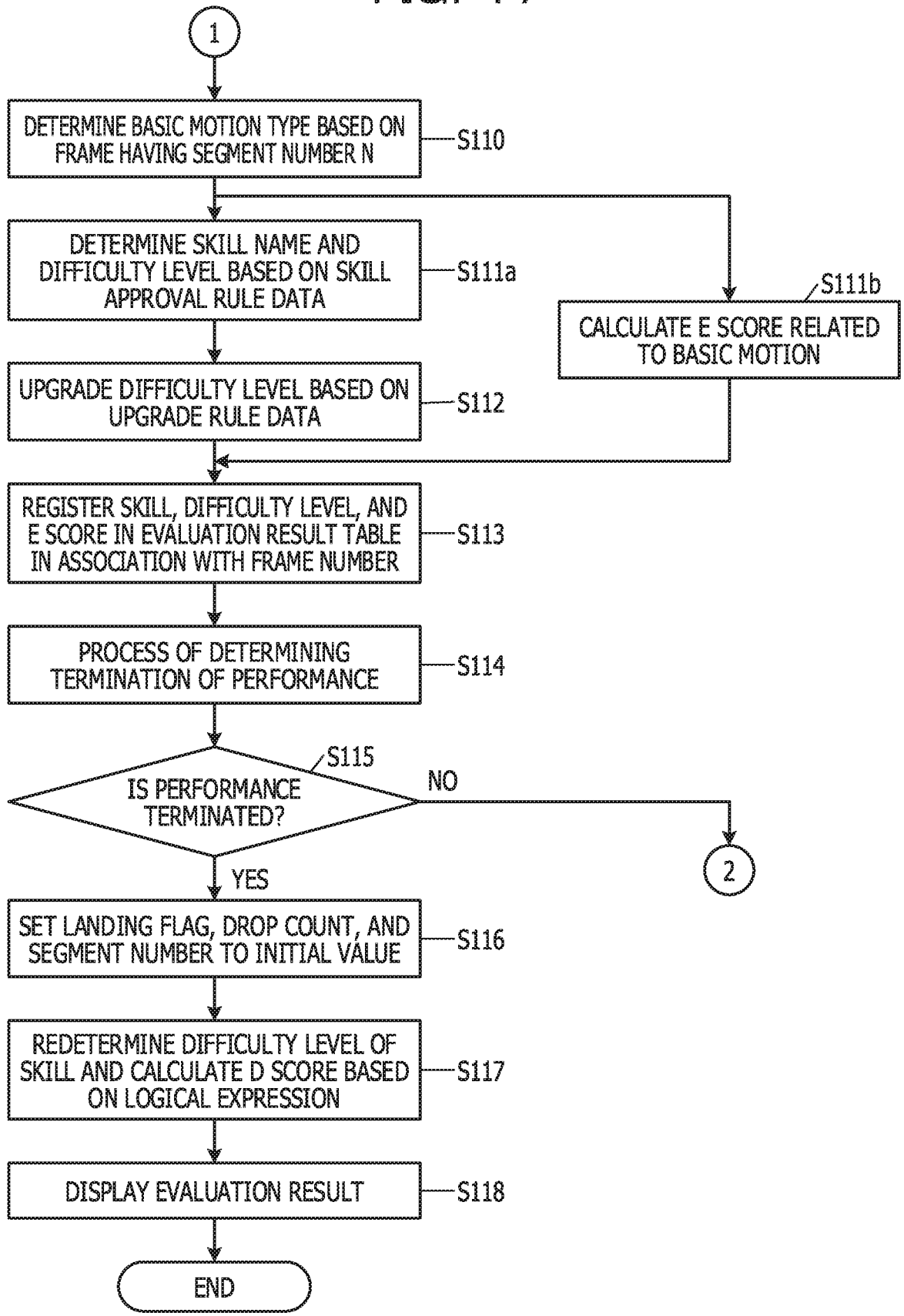
FIG. 17 is a flowchart (2) illustrating a process procedure of the motion recognition device.

Next, the process procedure of the motion recognition device 100 according to the present example will be described. FIGS. 16 and 17 are flowcharts illustrating the process procedure of the motion recognition device. As illustrated in FIG. 16, the motion recognition device 100 updates the frame number to be processed with a value obtained by adding 1 to the frame number (step S101). The calculation unit 152 of the motion recognition device 100 reads the skeleton data 141 (step S102).

The calculation unit 152 calculates the hand and foot position data and the body vector data based on the skeleton data 141 (step S103). The segmentation unit 153 of the motion recognition device 100 sets a front surface support flag (step S104). In step S104, the segmentation unit 153 sets the front surface support flag to "1" in a case where all of the above-described conditions A1, A2, and A3 are satisfied. In a case where all of the conditions A1, A2, and A3 are not satisfied, the segmentation unit 153 sets the front surface support flag to "0". The front surface support flag is associated with the frame number to be processed.

The segmentation unit 153 sets a landing flag (step S105). In step S105, the segmentation unit 153 sets the landing flag to "1" in a case where the position of the tip of the left toe (left ankle) or the position of the right foot (right ankle) of the subject 5 is less than a predetermined threshold value. The segmentation unit 153 sets the landing flag to "0" in a case where the position of the tip of the left toe (left ankle) or the position of the right foot (right ankle) of the subject 5 is equal to or greater than a predetermined threshold value. The landing flag is associated with the frame number to be processed.

The segmentation unit 153 performs segment point determination process (step S106). In step S106, in a case where the front surface support flag that corresponds to the previous frame number is "0" and the front surface support flag that corresponds to the frame number to be processed is "1", the segmentation unit 153 determines that the frame that corresponds to the frame number to be processed is a segment point. In a case where the front surface support flag that corresponds to the previous frame number is "1" and the front surface support flag that corresponds to the frame number to be processed is "0", the segmentation unit 153 determines that the frame that corresponds to the frame number to be processed is not a segment point.

In a case where it is determined that the frame is not a segment point (No in step S107), the segmentation unit 153 registers the hand and foot position data, the body vector data, and the current segment number in the calculation result data 142 in association with the frame number (step S108), and proceeds to step S101.

In a case where it is determined that that the frame is a segment point (Yes in step S107), the segmentation unit 153 updates the current segment number (step S109) and proceeds to step S110 in FIG. 17.

The identification unit 154 of the motion recognition device 100 determines the basic motion type based on the frame of the segment number n (step S110). The first evaluation unit 155 of the motion recognition device 100 determines the skill name and the difficulty level based on the skill approval rule data 143 (step S111a). The upgrade unit 156 of the motion recognition device 100 upgrades the difficulty level based on the upgrade rule data 144 (step S112) and proceeds to step S113.

The second evaluation unit 157 of the motion recognition device 100 calculates the E score related to the basic motion (step S111b), and proceeds to step S113.

The motion recognition device 100 registers the skill, the difficulty level, and the E score in the evaluation result table 145 in association with the frame number (step S113).

The motion recognition device 100 performs performance termination determination process (step S114). In step S114, the motion recognition device 100 determines that the performance is terminated in a case where the group to which the skill belongs is a predetermined group. The motion recognition device 100 determines that the performance is terminated in a case where a value of a drop count that totaled the landing flags is equal to or greater than the predetermined number.

In a case where the performance is not terminated (No in step S115), the motion recognition device 100 moves to step S101 in FIG. 16. In a case where the performance is terminated (Yes in step S115), the motion recognition device 100 sets the landing flag, the drop count, and the segment number to initial values (step S116).

The first evaluation unit 155 of the motion recognition device 100 re-determines the difficulty level of the skill by using the evaluation result data 145 and the logical expression indicating a rule, and calculates the D score (step S117). The display control unit 158 of the motion recognition device 100 displays the evaluation result (step S118).

Figure 18:
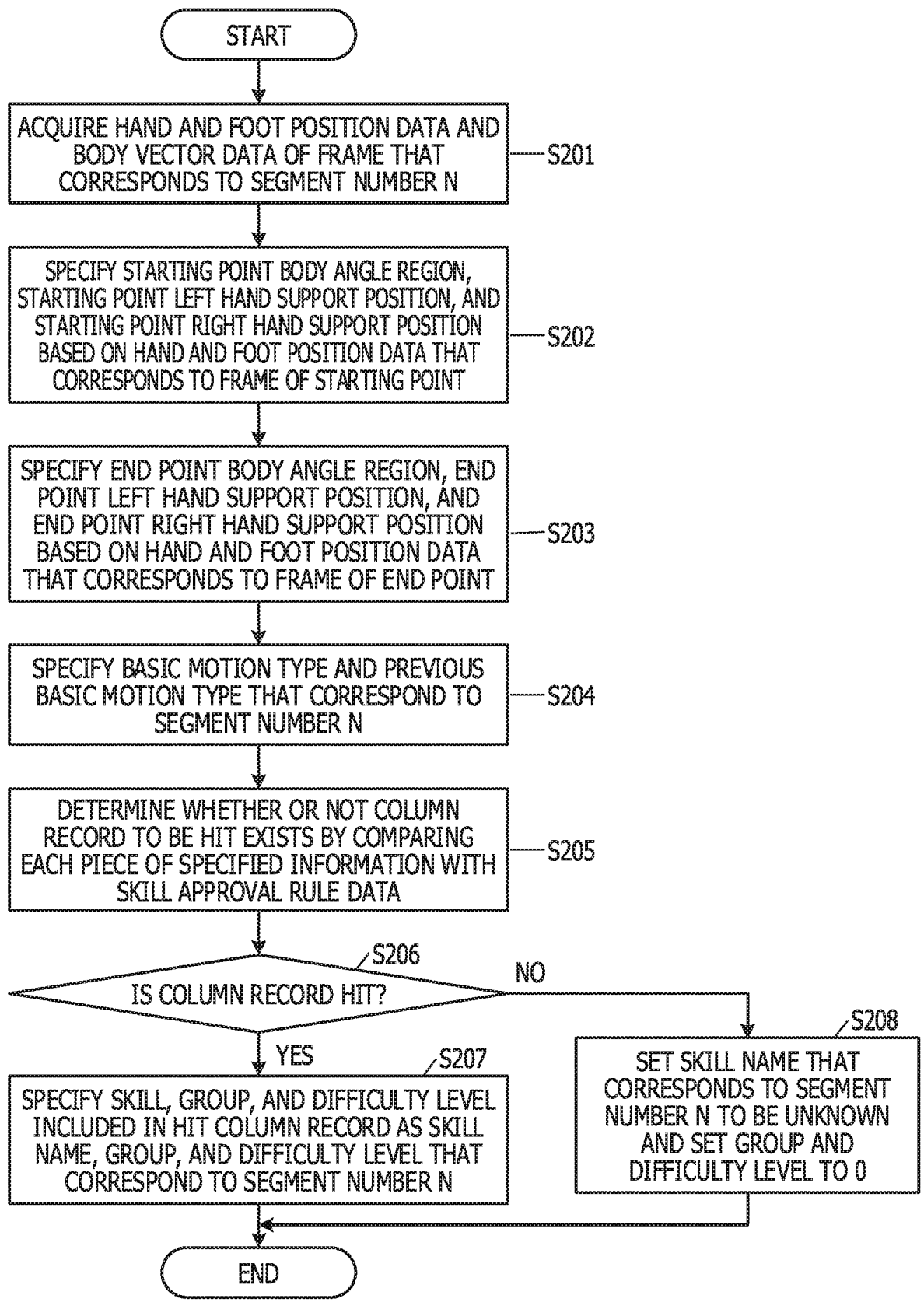
FIG. 18 is a flowchart illustrating a process procedure for determining a skill name and a difficulty level.

Next, an example of process for determining the skill name and the difficulty level based on the skill approval rule data described in step S111a of FIG. 17 will be described. FIG. 18 is a flowchart illustrating a process procedure for determining the skill name and the difficulty level. As illustrated in FIG. 18, the first evaluation unit 155 of the motion recognition device 100 acquires the hand and foot position data and the frame vector data of the frame that corresponds to the segment number n from the calculation result data 142 (step S201).

The first evaluation unit 155 specifies the starting point body angle region, the starting point left hand support position, the starting point right hand support position based on the hand and foot position data that corresponds to the frame at the starting point (step S202). The first evaluation unit 155 specifies the end point body angle region, the end point left hand support position, and the end point right hand support position based on the hand and foot position data that corresponds to the frame at the end point (step S203).

The first evaluation unit 155 specifies the basic motion type and the previous motion type that correspond to the segment number n (step S204).

The first evaluation unit 155 compares each piece of the specified information with the skill approval rule data 143, and determines whether or not a column record to be hit exists (step S205). Here, each piece of the specified information includes the starting point body angle region, the starting point left hand support position, the starting point right hand support position, the end point body angle region, the end point left hand support position, the end point right hand support position, the basic motion type, and the previous basic motion type.

In a case where the column record is hit (Yes in step S206), the first evaluation unit 155 specifies the skill name, the group, and the difficulty level n included in the hit column record as the skill name, the group, and the difficulty level that correspond to the segment number n (step S207). In a case where the column record is not hit (No in step S206), the first evaluation unit 155 sets the skill name that corresponds to the segment number n to be unknown and sets the group and the difficulty level to 0 (step S208).

Figure 19:
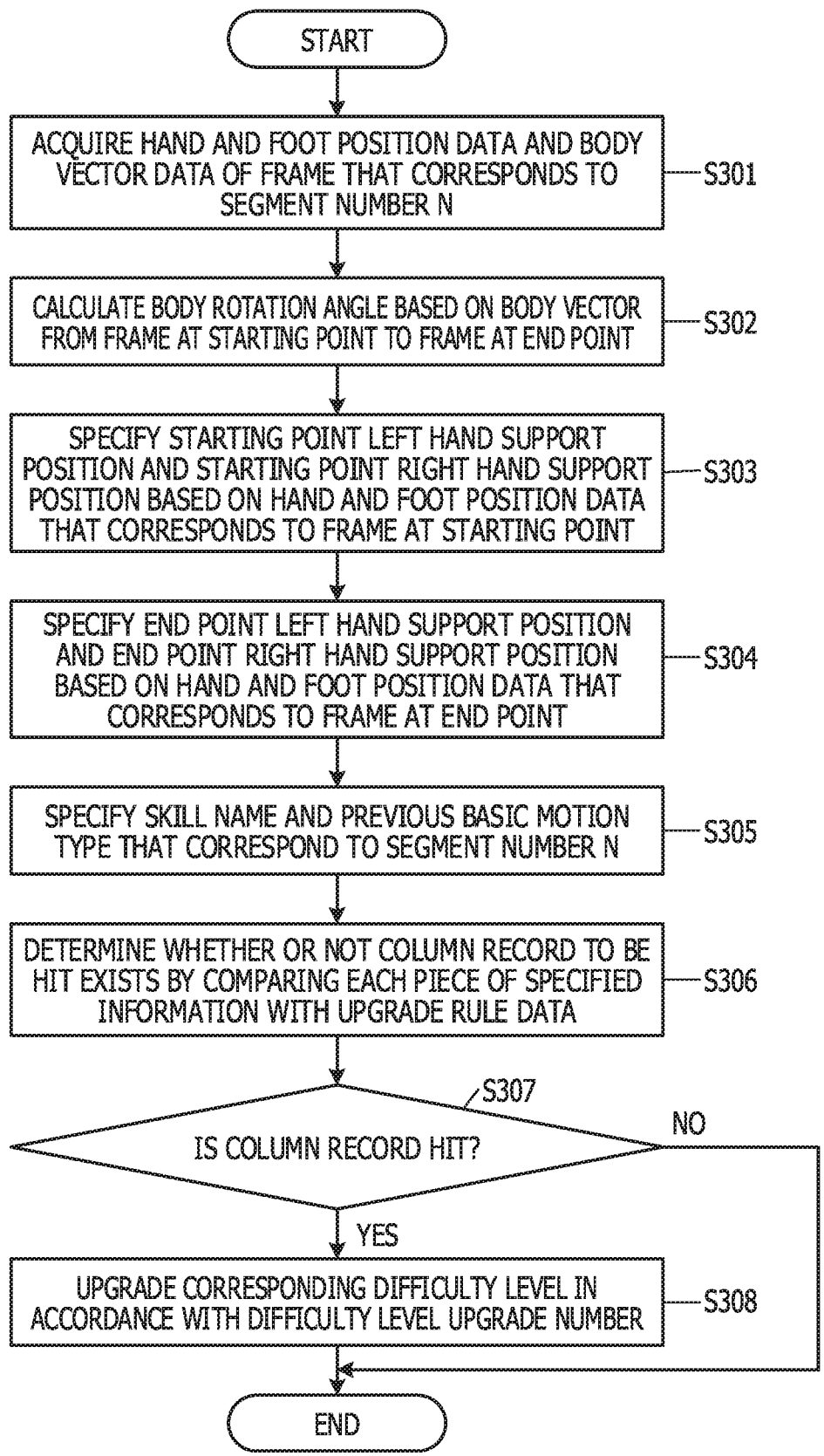
FIG. 19 is a flowchart illustrating a process procedure for upgrading the difficulty level.

Next, an example of process for upgrading the difficulty level based on the skill approval rule data described in step S112 of FIG. 17 will be described. FIG. 19 is a flowchart illustrating a process procedure for upgrading the difficulty level. As illustrated in FIG. 19, the upgrade unit 156 of the motion recognition device 100 acquires the hand and foot position data and the body vector data of the frame that corresponds to the segment number n from the calculation result data 142 (step S301).

The upgrade unit 156 calculates the body rotation angle based on the body vector from the frame at the starting point to the frame at the end point (step S302).

The upgrade unit 156 specifies the starting point left hand support position and the starting point right hand support position based on the hand and foot position data that corresponds to the frame at the starting point (step S303). The end point left hand support position and the end point right hand support position are specified based on the hand and foot position data that corresponds to the frame at the end point (step S304).

The upgrade unit 156 specifies the skill name and the previous motion type that correspond to the segment number n (step S305).

The upgrade unit 156 compares each piece of the specified information with the upgrade rule data 144, and determines whether or not the column record to be hit exists (step S306). In a case where the column record is hit (Yes in step S307), the upgrade unit 156 upgrades the difficulty level in accordance with the difficulty level upgraded number (step S308). In a case where the column record is not hit (No in step S307), the upgrade unit 156 terminates the process.

Figure 20:
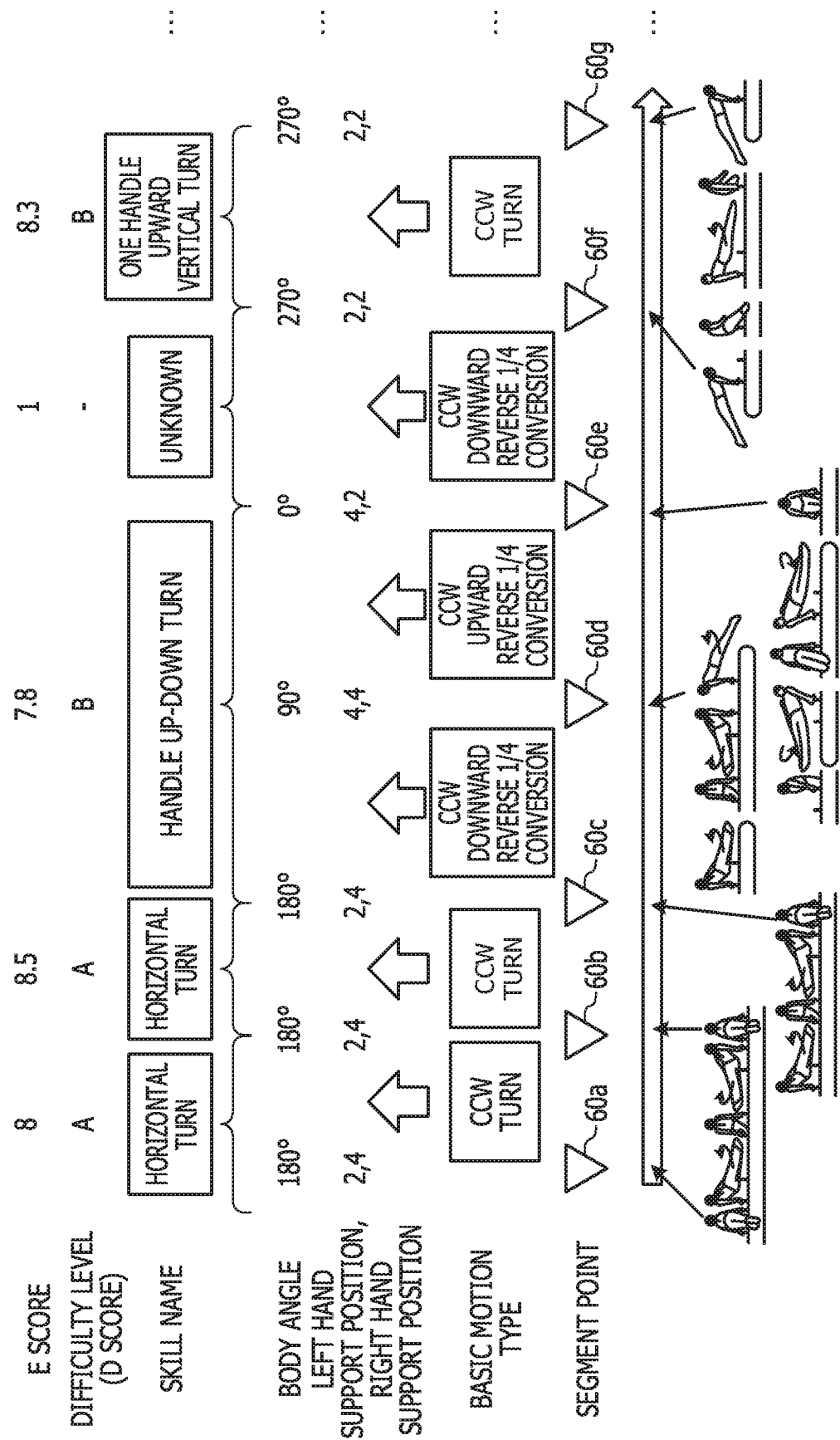
FIG. 20 is a view illustrating an example of a process of the motion recognition device.

FIG. 20 is a view illustrating an example of process of the motion recognition device. In the example illustrated in FIG. 20, the segmentation unit 153 sets segment points 60a to 60g based on the calculation result data 142. For example, in the frame of the segment points 60a, 60b, and 60c, the left hand support position of the subject 5 is "2" and the right hand support position is "4". In the frame of the segment point 60d, the left hand support position of the subject 5 is "4" and the right hand support position is "4". In the frame of the segment point 60e, the left hand support position of the subject 5 is "4" and the right hand support position is "2". In the frame of segment points 60f and 60g, the left hand support position of the subject 5 is "2" and the right hand support position is "2". In addition, in the frame of segment points 60a to 60g, although not being illustrated, it is assumed that the body vector is oriented downward.

As an example, the body angle of the frame of the segment points 60a, 60b, and 60c is 180°. The body angle of the frame of the segment point 60d is 90°. The body angle of the frame of the segment point 60e is 0°. The body angle of the frame of the segment points 60f and 60g is 270°.

As an example, the identification unit 154 determines the basic motion type as "CCW turn" from the movement of the feature points of each frame included in the segment points 60a to 60b. The identification unit 154 determines the basic motion type as "CCW turn" from the movement of the feature points of each frame included in the segment points 60b to 60c. The identification unit 154 determines the basic motion type as "CCW downward reverse ¼ conversion" from the movement of the feature points of each frame included in the segment points 60c to 60d. The identification unit 154 determines the basic motion type as "CCW upward reverse ¼ conversion" from the movement of the feature points of each frame included in the segment points 60d to 60e. The identification unit 154 determines the basic motion type as "CCW downward reverse ¼ turn" from the movement of the feature points of each frame included in the segment points 60e to 60f. The identification unit 154 determines the basic motion type as "CCW turn" from the movement of the feature points of each frame included in the segment points 60f to 60g.

For example, the first evaluation unit 155 determines the skill name performed by the subject between each frame included in the segment points 60a to 60b as "horizontal turn" and the difficulty level "A", based on the skill approval rule data 143. The first evaluation unit 155 determines the skill name performed by the subject between each frame included in the segment points 60b to 60c as "horizontal turn" and the difficulty level "A", based on the skill approval rule data 143. The first evaluation unit 155 determines the skill name performed by the subject between each frame included in the segment points 60c to 60e as "handle up-down conversion" and the difficulty level "B", based on the skill approval rule data 143. The first evaluation unit 155 determines the skill name "unknown" and the difficulty level "–" without setting the skill name and the difficulty level performed by the subject between each frame included in the segment points 60e to 60f, based on the skill approval rule data 143. The first evaluation unit 155 determines the skill name performed by the subject between each frame included in the segment points 60f to 60g as "one handle upward vertical turn" and the difficulty level "B", based on the skill approval rule data 143.

As an example, the second evaluation unit 157 determines that the E score of the performance performed by the subject between each frame included in the segment points 60a to 60b is "8". The second evaluation unit 157 determines that the E score of the performance performed by the subject between each frame included in the segment points 60b to 60c is "8.5". The second evaluation unit 157 determines that the E score of the performance performed by the subject between each frame included in the segment points 60c to 60e is "7.8". The second evaluation unit 157 determines that the E score of the performance performed by the subject between the frames included in the segment points 60e to 60f is "1". The second evaluation unit 157 determines that the E score of the performance performed by the subject between each frame included in the segment points 60f to 60g is "8.3".

Next, the effect of the motion recognition device 100 according to the present example will be described. Based on the skeleton data 141 of the subject 5, the motion recognition device 100 specifies a frame that serves as a segment point and classifies the frame into a plurality of pieces of partial data. The motion recognition device 100 specifies the basic motion type of each piece of partial data, and evaluates the skill number and the difficulty level of the motion performed by the subject based on the order of the basic motion types of the partial data which is consecutive in time series. In this manner, in order to evaluate the skill name and the difficulty level based on the order of the basic motion type, according to the motion recognition device 100, the performance of the subject 5 may be evaluated efficiently.

The motion recognition device 100 upgrades the difficulty level of the motion based on the order and the body rotation angle of the basic motion type of the partial data which is consecutive in time series. Therefore, it is possible to specify an accurate difficulty level that corresponds to complicated evaluation criteria of competition.

The motion recognition device 100 calculates the E score that corresponds to the partial data based on the evaluation criterion that associates the features at the feature points of each frame included in the partial data with the score. Therefore, in addition to the skill and the difficulty level, the E score may also be calculated appropriately.

The motion recognition device 100 specifies a frame in which the body vector is oriented downward and both hands of the subject 5 are positioned in a predetermined region as a segment point. Therefore, it is possible to appropriately segment a plurality of frames, and it is possible to improve the determination accuracy of the skill or the difficulty level.

However, the calculation unit 152 of the motion recognition device 100 according to the present example performs calculation by using the normal vector 7 of the plane 6 that passes through the feature point 5b of the right shoulder function, the feature point 5e of the right shoulder joint, and the feature point 5i in the back as a body vector, but the present invention is not limited thereto.

Figure 21:
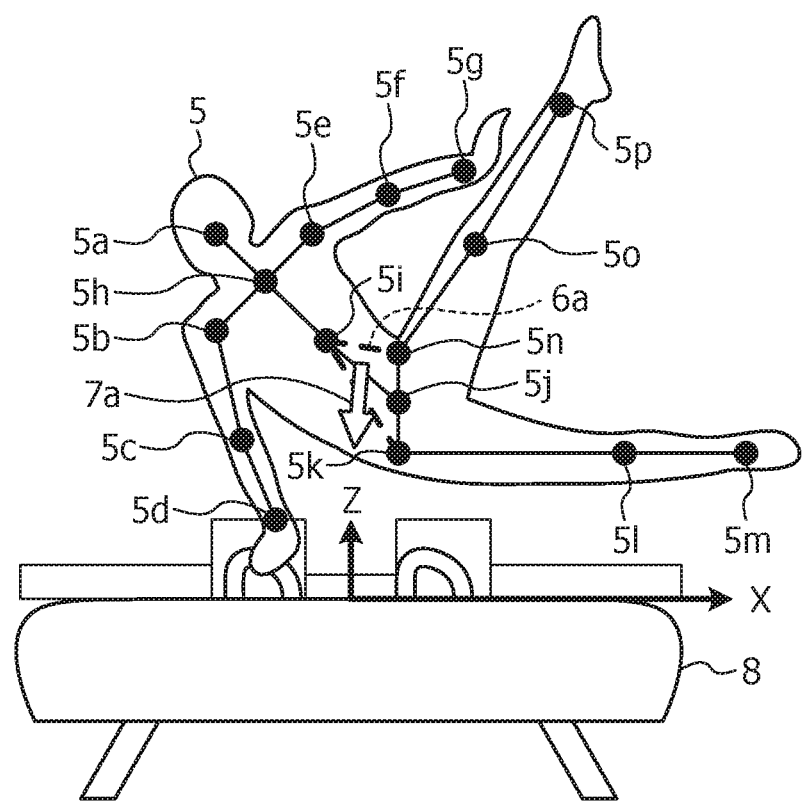
FIG. 21 is a view for describing an example of another body vector.

FIG. 21 is a view for describing an example of another body vector. The calculation unit 152 may perform calculation by using the normal vector 7a of the plane 6a that passes through the feature points 5k and 5n of each hip joint (right hip joint, left hip joint) and the feature point 5i of the back as a body vector. In addition, the direction of the normal vector 7a is taken as the ventral side of the subject 5, and the magnitude of the normal vector 7a is set to "1". In the following description, the normal vector 7a is expressed as the body vector 7a. The starting point of the body vector 7a may be in any place as long as the starting point is fixed onto the plane (triangle) 6a, but may be the midpoint of the feature points 5k and 5n or the center of gravity of the plane 6a. Even in a case where the body vector 7a is used instead of the body vector 7, the segmentation unit 153 may appropriately segment the plurality of frames and improve the determination accuracy of the skill or the difficulty level. Furthermore, the body vector 7a is appropriate for evaluating the orientation of the lower part of the trunk compared with the body vector 7.

In addition, the calculation unit 152 may adjust or estimate the position coordinates of the feature points 5b, 5e, 5i, 5k, and 5n by inverse kinematics calculation using the entire feature point position coordinates so as to match the actual motion of the subject 5, and may calculate the body vector 7 and the body vector 7a. The calculation unit 152 may employ the unit normal vector of the plane 6 of the adjusted or estimated feature points 5b, 5e, and 5i or the plane 6a of the adjusted or estimated feature points 5i, 5k, and 5n, as the body vector. In this manner, by employing the body vectors 7 and 7a which are adjusted or estimated and calculated so as to make the position coordinates of each of the feature points 5b, 5e, 5i, 5k, and 5n, due to the reason, such as occlusion, it is possible to correspond to a case where it is not possible to directly detect the feature point of the subject 5 or a case where the error of the position of the feature point becomes large, and the determination accuracy of the skill may be improved.

Figure 22:
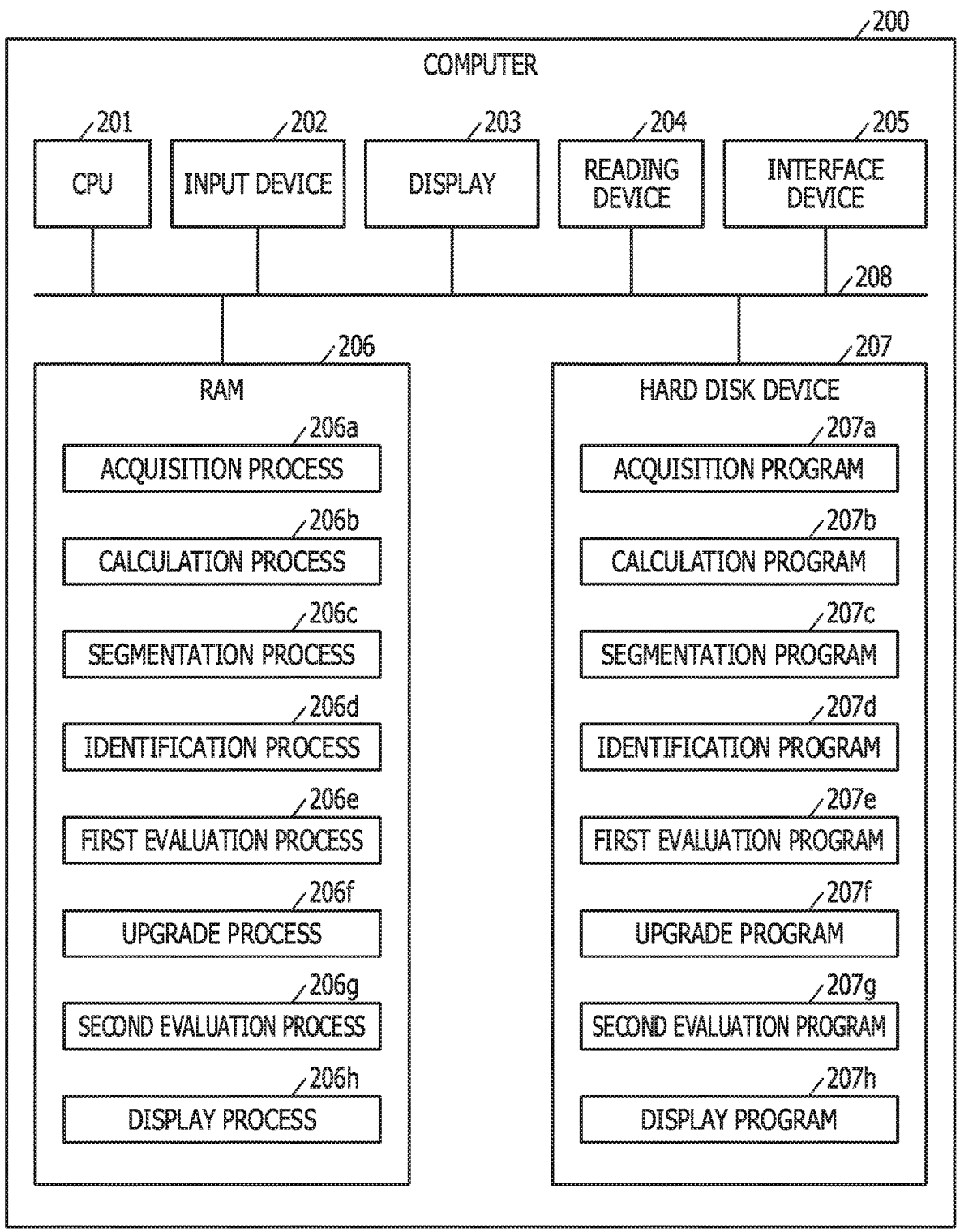
FIG. 22 is a view illustrating an example of a hardware configuration of a computer that realizes a function similar to that of the motion recognition device.

Next, an example of a hardware configuration of a computer that realizes a function similar to that of the motion recognition device 100 illustrated in the above-described example will be described. FIG. 22 is a view illustrating an example of the hardware configuration of the computer that realizes the function similar to that of the motion recognition device.

As illustrated in FIG. 22, the computer 200 includes a CPU 201 that executes various arithmetic process, an input device 202 that receives the input of the data from a user, and a display 203. Furthermore, the computer 200 includes a reading device 204 for reading a program or the like from a storage medium, and an interface device 205 for exchanging the data with another computer via a network. The computer 200 acquires the skeleton data from the skeleton recognition device 20 via the interface device 205. Further, the computer 200 includes a RAM 206 for temporarily storing various pieces of information, and a hard disk device 207. In addition, each of the devices 201 to 207 is connected to the bus 208.

The hard disk device 207 has an acquisition program 207a, a calculation program 207b, a segmentation program 207c, an identification program 207d, a first evaluation program 207e, an upgrade program 207f, a second evaluation program 207g, and a display program 207h. The CPU 201 reads out each of the programs 207a to 207h and develops the programs in the RAM 206.

The acquisition program 207a functions as an acquisition process 206a. The calculation program 207b functions as a calculation process 206b. The segmentation program 207c functions as a segmentation process 206c. The identification program 207d functions as an identification process 206d. The first evaluation program 207e functions as a first evaluation process 206e. The upgrade program 207f functions as an upgrade process 206f. The second evaluation program 207g functions as a second evaluation process 206g. The display program 207h functions as a display process 206h.

The process of the acquisition process 206a corresponds to the process of the acquisition unit 151. The process of the calculation process 206b corresponds to the process of the calculation unit 152. The process of the segmentation process 206c corresponds to the process of the segmentation unit 153. The process of the identification process 206d corresponds to the process of the identification unit 154. The process of the first evaluation process 206e corresponds to the process of the first evaluation unit 155. The process of the upgrade process 206f corresponds to the process of the upgrade unit 156. The process of the second evaluation process 206g corresponds to the process of the second evaluation unit 157. The process of the display process 206h corresponds to the process of the display control unit 158.

In addition, each of the programs 207a to 207h do not necessarily have to be stored in the hard disk device 207 from the beginning. For example, each program is stored in "portable physical medium", such as a flexible disk (FD), a CD-ROM, a DVD disk, a magnetooptical disk, an IC card or the like inserted into the computer 200. In addition, the computer 200 may read out and execute each of the programs 207a to 207h.

The skill names in the specification may replaced by the skill names defined by the gymnastics.

All examples and conditional language provided herein are intended for the pedagogical purposes of aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although one or more embodiments of the present invention have been described in detail, it should be understood that the various changes, substitutions, and alterations could be made hereto without departing from the spirit and scope of the invention.

What is claimed is:

1. A motion recognition device comprising:
a memory; and
a processor coupled to the memory and configured to:
classify a plurality of frames including positional information of a feature point that corresponds to a predetermined part or a joint part of a body of a subject into a plurality of groups in time series by segmenting the plurality of frames in time series based on a position of the predetermined part of the body of the subject;
identify, for a respective group, a type of a basic motion that corresponds to the respective group, based on movement of the feature point included in a consecutive frame; and
evaluate, for the respective group, a skill and a difficulty level of the movement indicated by the respective group, by using a criteria identified by both of a first basic motion type and a second basic motion type, the first basic motion type being the type of the basic motion identified for the respective group, the second basic motion type being the type of the basic motion identified for a group one before the respective group,
wherein the evaluating is configured to evaluate, for each group, a score of the respective group by comparing features of the feature points included in the frame of the respective group with evaluation criteria, the evaluation criterion being information indicating a respective score corresponding to each feature indicated by feature points to be included in frames.

2. The motion recognition device according to claim 1, the processor further configured to:
in response to performing of the evaluating, upgrade a value corresponding to the evaluated difficulty level of the motion performed by the subject based on the order of the basic motion that corresponds to the group which is consecutive in time series and a rotation angle of the body of the subject.

3. The motion recognition device according to claim 1, the processor further configured to:
repeatedly execute a process of determining a frame that serves as a segment point based on a direction of a normal vector of a plane that passes through both shoulders and a back of the subject and the positions of both hands of the subject, and classifies the plurality of frames sandwiched between the frames that serve as the segment points into one group.

4. The motion recognition device according to claim 1, the processor further configured to:

repeatedly execute a process of determining a frame that serves as a segment point based on a direction of a normal vector of a plane that passes through both hip joints and a back of the subject and the positions of both hands of the subject, and classifies the plurality of frames sandwiched between the frames that serve as the segment points into one group.

5. A motion recognition method of which a process is executed by a computer, the process comprising:

classifying a plurality of frames including positional information of a feature point that corresponds to a predetermined part or a joint part of a body of a subject into a plurality of groups in time series by segmenting the plurality of frames in time series based on a position of the predetermined part of the body of the subject, identifying, for a respective group, a type of a basic motion that corresponds to the respective group, based on movement of the feature point included in a consecutive frame; and evaluating, for the respective group, a skill and a difficulty level of the movement indicated by the respective group, by using a criteria identified by both of a first basic motion type and a second basic motion type, the first basic motion type being the type of the basic motion identified for the respective group, the second basic motion type being the type of the basic motion identified for a group one before the respective group, wherein the evaluating is configured to evaluate, for each group, a score of the respective group by comparing features of the feature points included in the frame of the respective group with evaluation criteria, the evaluation criterion being information indicating a respective score corresponding to each feature indicated by feature points to be included in frames.

6. The motion recognition method according to claim 5, wherein in response to performing of the evaluating, upgrading a value corresponding to the evaluated difficulty level of the motion performed by the subject based on the order of the basic motion that corresponds to the group which is consecutive in time series and a rotation angle of the body of the subject.

7. The motion recognition method according to claim 5, wherein in the process of classifying, a process of determining a frame that serves as a segment point is repeatedly executed based on a direction of a normal vector of a plane that passes through both shoulders and a back of the subject and the positions of both hands of the subject, and the plurality of frames sandwiched between the frames that serve as the segment points are classified into one group.

8. The motion recognition method according to claim 5, wherein in the process of classifying, a process of determining a frame that serves as a segment point is repeatedly executed based on a direction of a normal vector of a plane that passes through both hip joints and a back of the subject and the positions of both hands of the subject, and the plurality of frames sandwiched between the frames that serve as the segment points are classified into one group.

9. A non-transitory computer-readable storage medium storing a motion recognition program that causes a computer to execute a process, the process comprising:

classifying a plurality of frames including positional information of a feature point that corresponds to a predetermined part or a joint part of a body of a subject into a plurality of groups in time series by segmenting the plurality of frames in time series based on a position of the predetermined part of the body of the subject;

identifying, for a respective group, a type of a basic motion that corresponds to the respective group, based on movement of the feature point included in a consecutive frame; and evaluating, for the respective group, a skill and a difficulty level of the movement indicated by the respective group, by using a criteria identified by both of a first basic motion type and a second basic motion type, the first basic motion type being the type of the basic motion identified for the respective group, the second basic motion type being the type of the basic motion identified for a group one before the respective group, wherein the evaluating is configured to evaluate, for each group, a score of the respective group by comparing features of the feature points included in the frame of the respective group with evaluation criteria, the evaluation criterion being information indicating a respective score corresponding to each feature indicated by feature points to be included in frames.

10. The non-transitory computer-readable storage medium according to claim 9, the process further comprising:

in response to performing of the evaluating, upgrading a value corresponding to the evaluated difficulty level of the motion performed by the subject based on the order of the basic motion that corresponds to the group which is consecutive in time series and a rotation angle of the body of the subject.

11. The non-transitory computer-readable storage medium according to claim 9, wherein in the process of classifying, a process of determining a frame that serves as a segment point is repeatedly executed based on a direction of a normal vector of a plane that passes through both shoulders and a back of the subject and the positions of both hands of the subject, and the plurality of frames sandwiched between the frames that serve as the segment points are classified into one group.

12. The non-transitory computer-readable storage medium according to claim 9, wherein in the process of classifying, a process of determining a frame that serves as a segment point is repeatedly executed based on a direction of a normal vector of a plane that passes through both hip joints and a back of the subject and the positions of both hands of the subject, and the plurality of frames sandwiched between the frames that serve as the segment points are classified into one group.

* * * * *